United States Patent [19]
Schleger et al.

[11] Patent Number: 5,907,868
[45] Date of Patent: Jun. 1, 1999

[54] FACIAL SHIELD, PARTICULARLY FOR PROTECTION FROM THE SUN

[75] Inventors: Linda Schleger, Kings Point; Mary Wittman, Great Neck, both of N.Y.

[73] Assignees: Hubert Greenway, Rancho Santa Fe; Steven Pratt, La Jolla, both of Calif.

[21] Appl. No.: 08/959,715

[22] Filed: Oct. 28, 1997

Related U.S. Application Data

[63] Continuation of application No. 08/366,895, Dec. 30, 1994, abandoned, which is a continuation of application No. 08/055,040, Apr. 29, 1993, Pat. No. 5,379,464, which is a continuation-in-part of application No. 07/919,587, Jul. 24, 1992, Pat. No. 5,379,463.

[51] Int. Cl.$^6$ ........................................................ A61F 9/02
[52] U.S. Cl. .......................... 2/10; 2/431; 2/449; 351/47; 351/88; 351/155
[58] Field of Search ................................ 2/11, 12, 13, 15, 2/426, 431, 432, 445, 446, 448, 449, 450, 451, 453, 454, 447, 427, 10; 351/41, 44, 45, 47, 59, 87, 88, 111, 131, 155

[56] References Cited

U.S. PATENT DOCUMENTS

| | | | |
|---|---|---|---|
| 2,026,741 | 1/1936 | Kintz . | |
| 2,519,561 | 8/1950 | Gillman et al. . | |
| 3,298,031 | 1/1967 | Morgan . | |
| 3,383,707 | 5/1968 | McNeill | 2/12 |
| 3,384,903 | 5/1968 | Malcom, Jr. | 2/14 |
| 3,678,929 | 7/1972 | Buscher . | |
| 4,541,125 | 9/1985 | Phillips | 2/10 |
| 4,730,915 | 3/1988 | Jannard | 351/47 |
| 4,869,586 | 9/1989 | Chung | 2/10 |
| 5,012,527 | 5/1991 | Michel . | |
| 5,208,916 | 5/1993 | Kelman | 2/10 |
| 5,220,689 | 6/1993 | Miller | 2/12 |
| 5,261,124 | 11/1993 | Day | 2/10 |
| 5,373,583 | 12/1994 | Birum | 2/10 |
| 5,422,686 | 6/1995 | Kelman et al. | 2/10 |

FOREIGN PATENT DOCUMENTS

| | | |
|---|---|---|
| 0293593 | 7/1988 | European Pat. Off. . |
| 721069 | 2/1932 | France . |

*Primary Examiner*—Michael A. Neas
*Attorney, Agent, or Firm*—Ostrolenk, Faber, Gerb & Soffen, LLP

[57] ABSTRACT

Facial protective wear including a facial shield member having a substantially transparent portion for allowing visible light to pass to the wearer's eyes and a support coupled to the facial shield for supporting the facial shield on the wearer's head. The facial shield member further has a nose protective portion extending over and protecting substantially the wearer's entire nose from in front of and from above and preferably has side portions protecting the wearer's eyes in a direction from the sides of the wearer's head. The facial shield member transparent portion preferably substantially prevents ultraviolet solar radiation from reaching the wearer's eyes and facial features, such as the nose and cheeks, and also from reaching the eyes in a direction from the sides of the head. The facial protective wear also can be used to protect the wearer from the wind and from injury due to flying objects. Various embodiments are described, including embodiments that clip onto existing eyewear or headware. The nose protective portion can be made integrally with the transparent shield portion or removable.

10 Claims, 22 Drawing Sheets

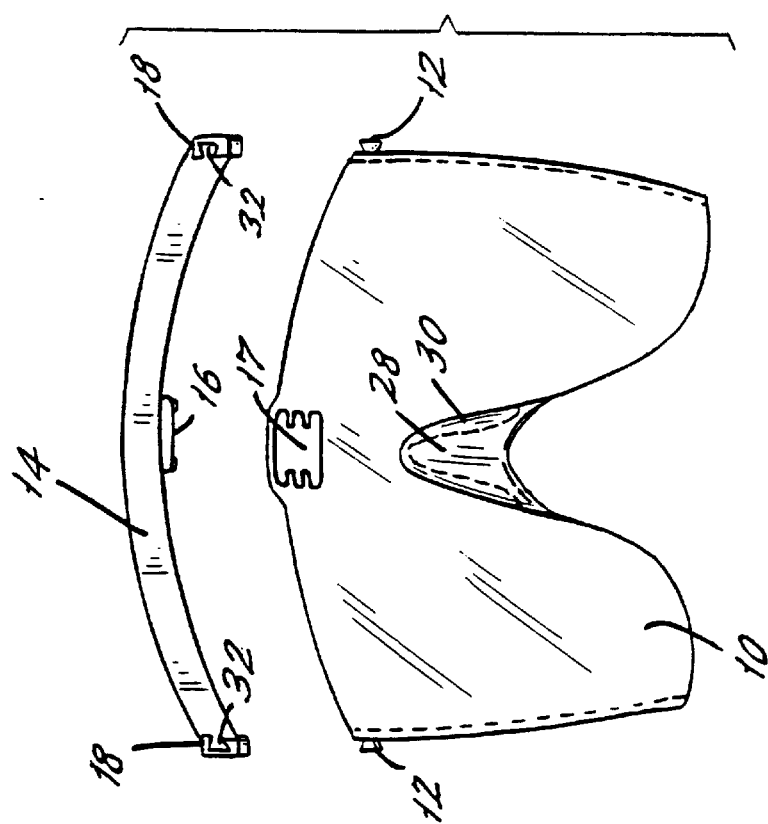
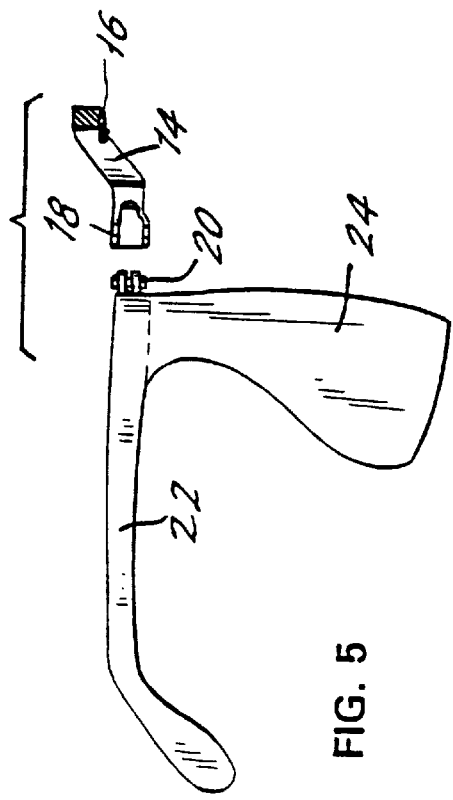
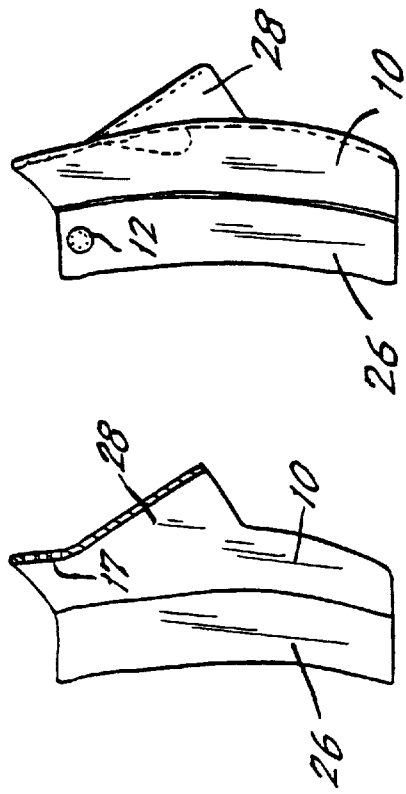

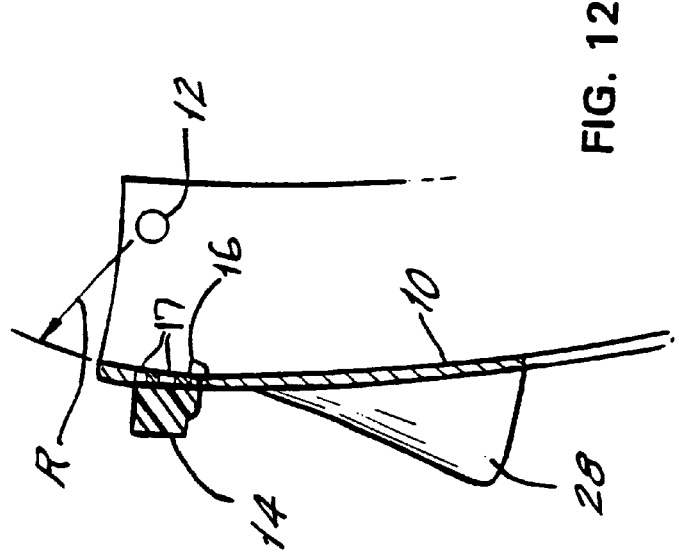
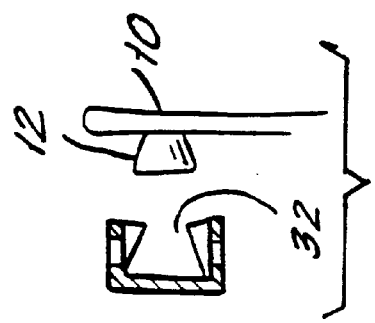
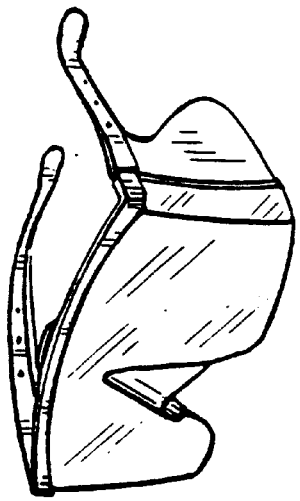
FIG. 9
FIG. 10
FIG. 11
FIG. 12

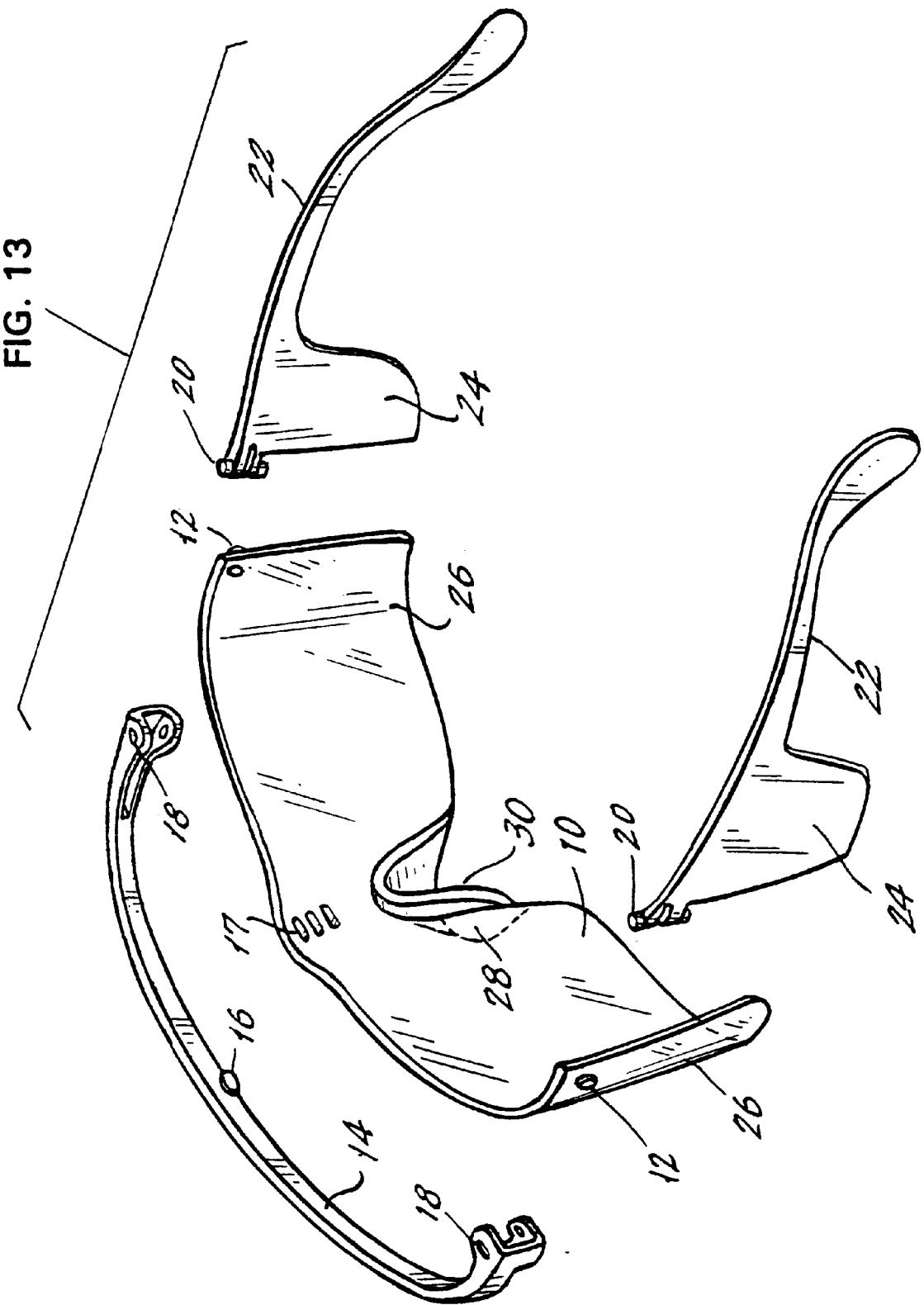

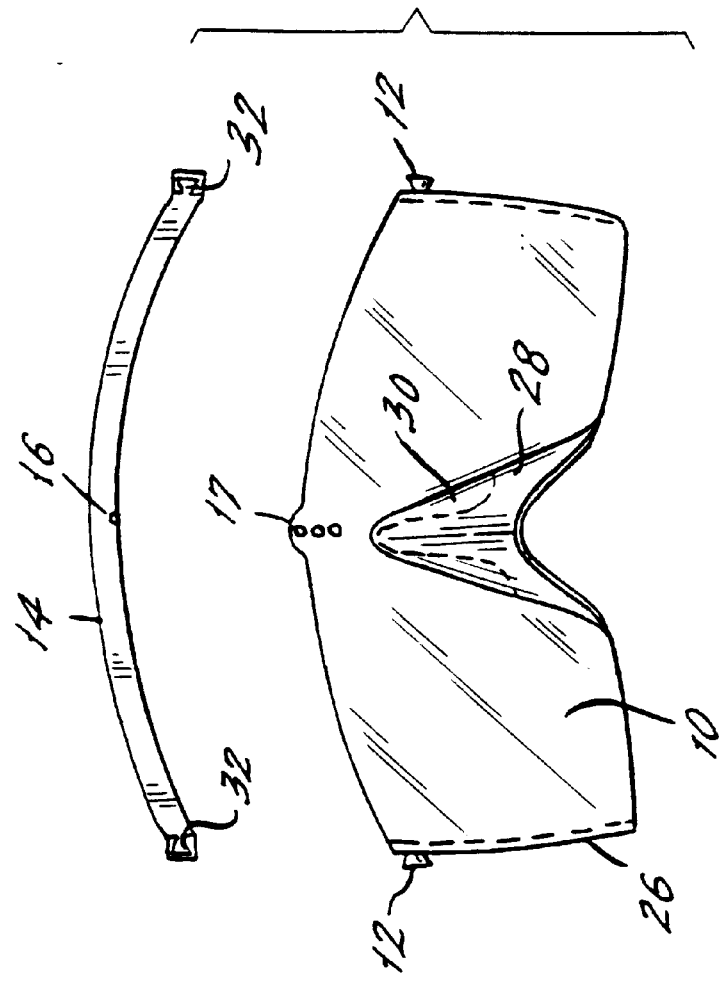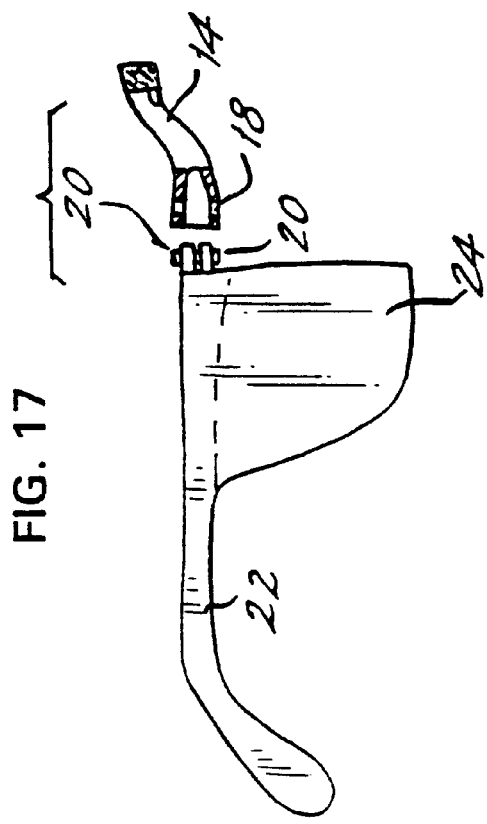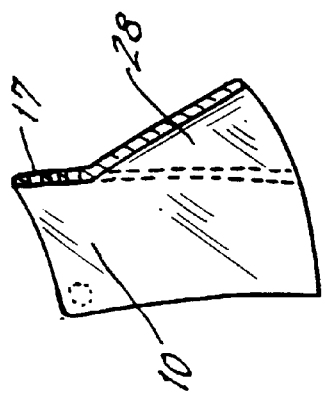
FIG. 17
FIG. 18
FIG. 19

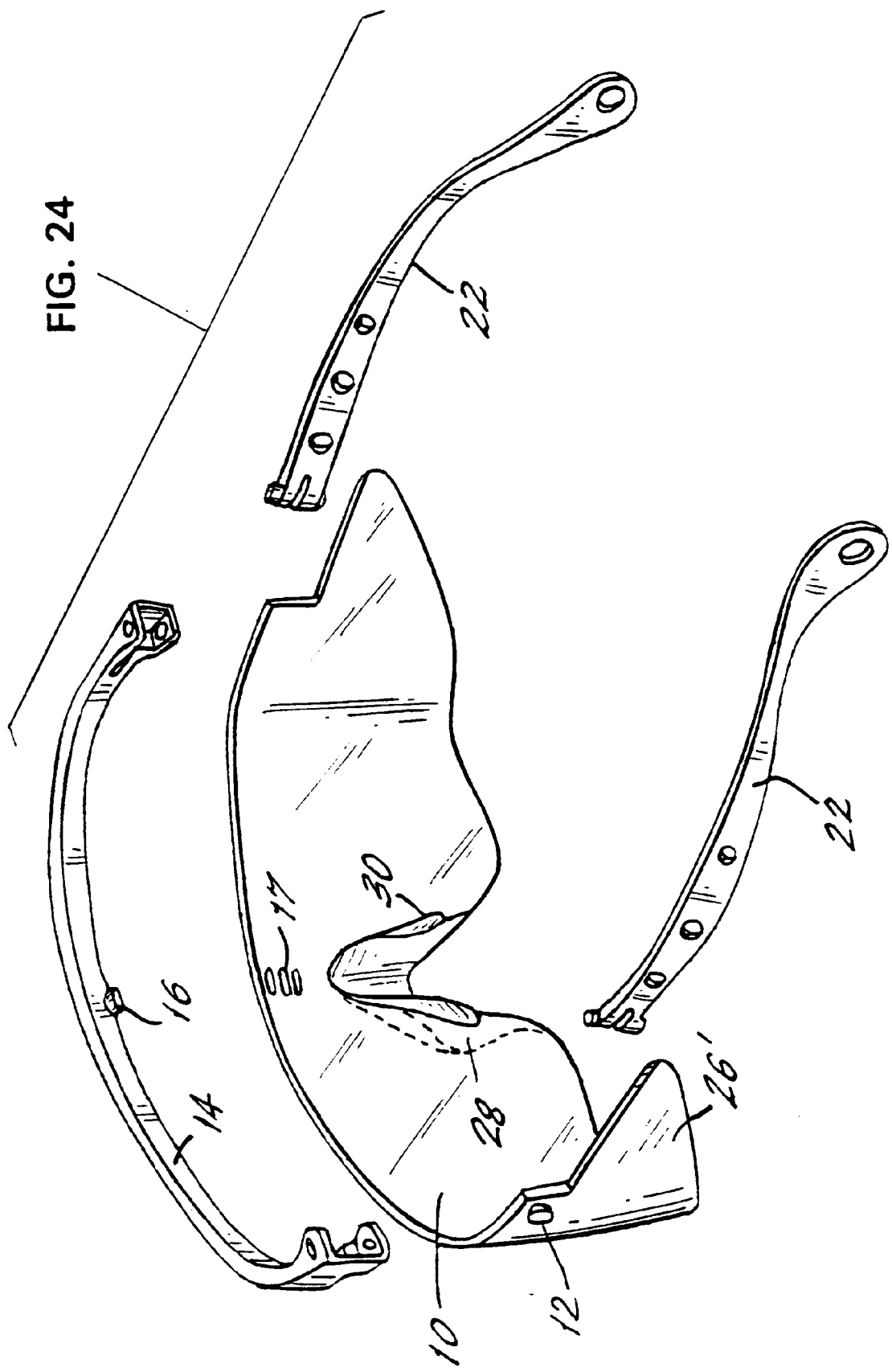

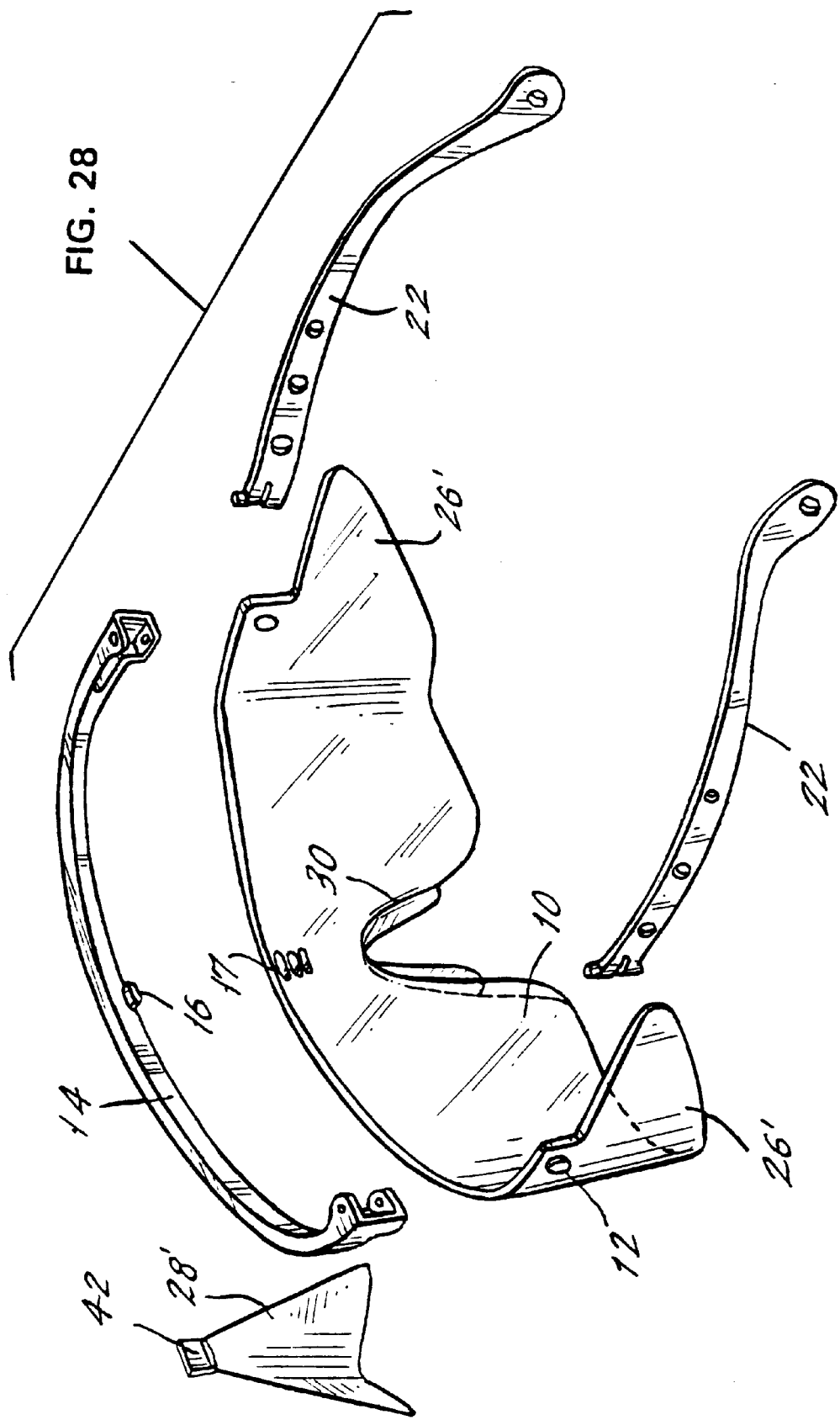

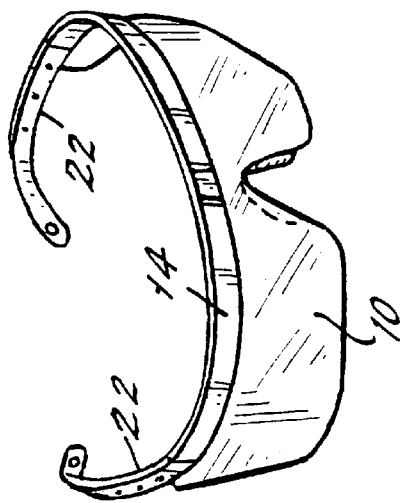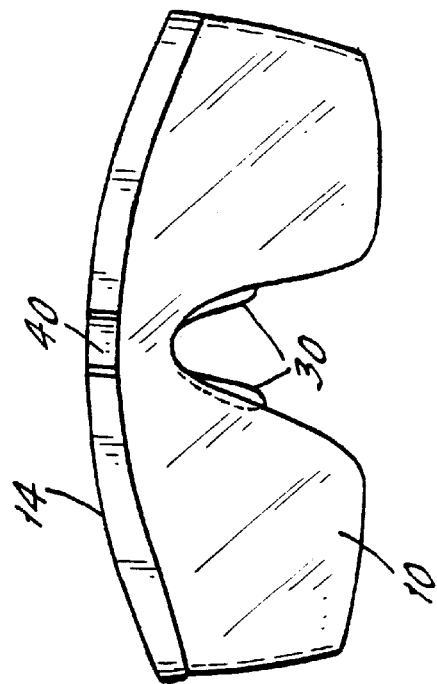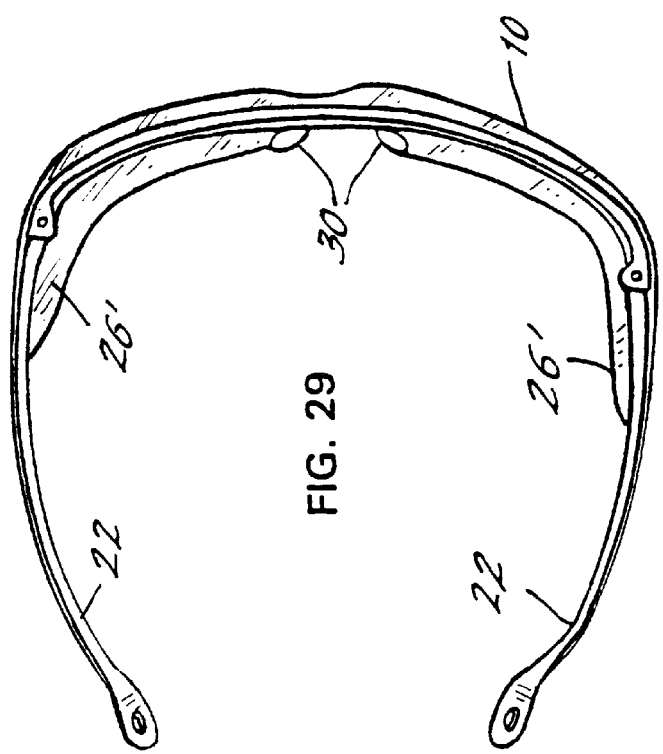

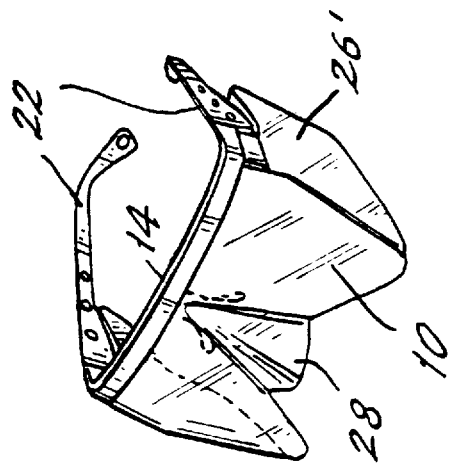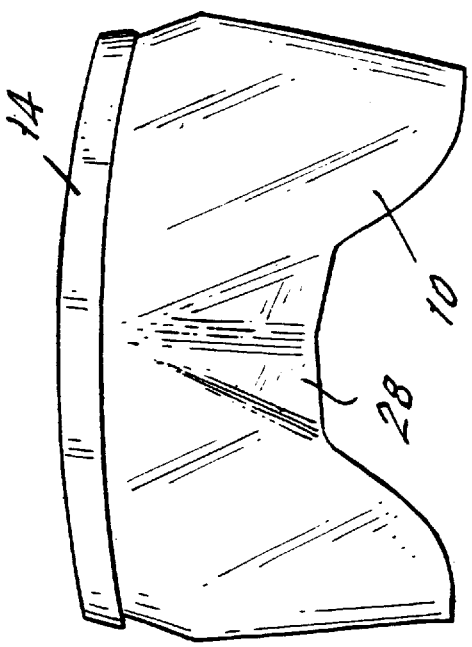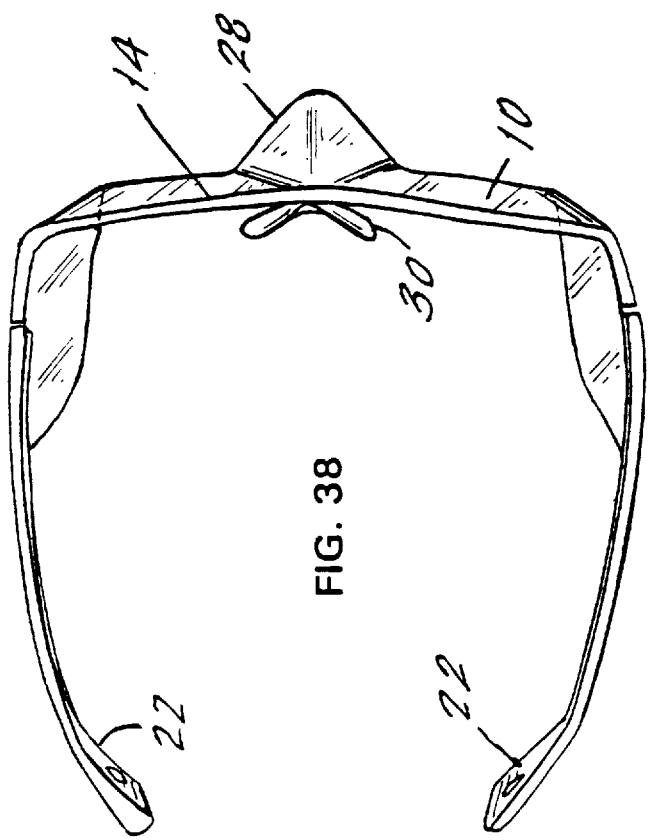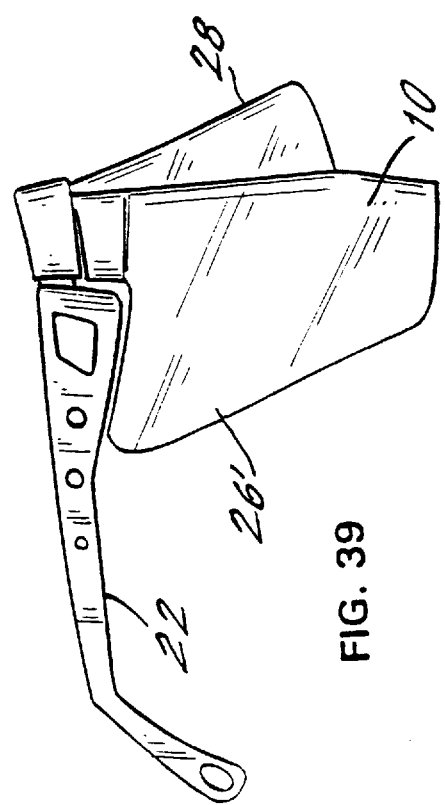

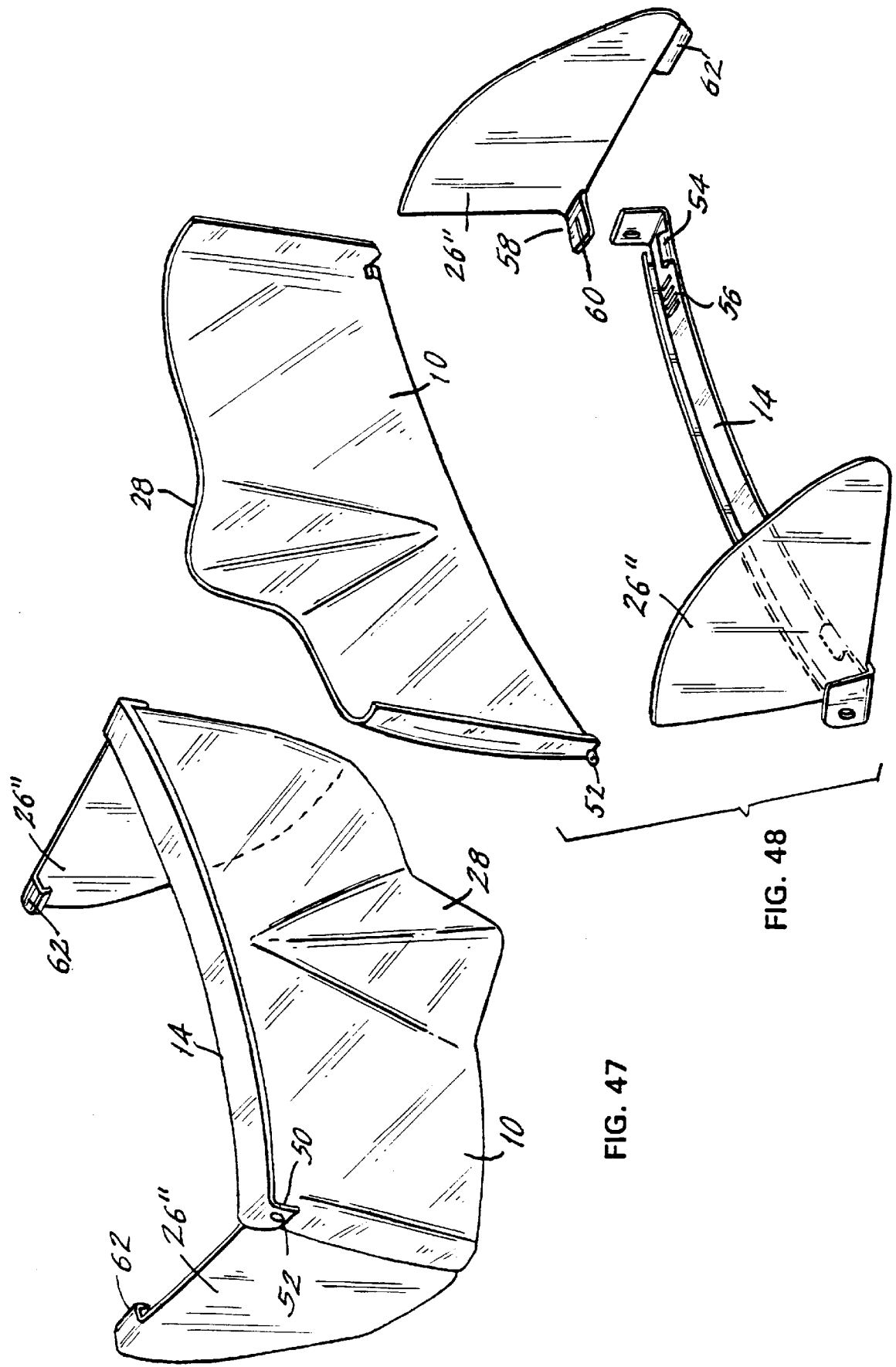

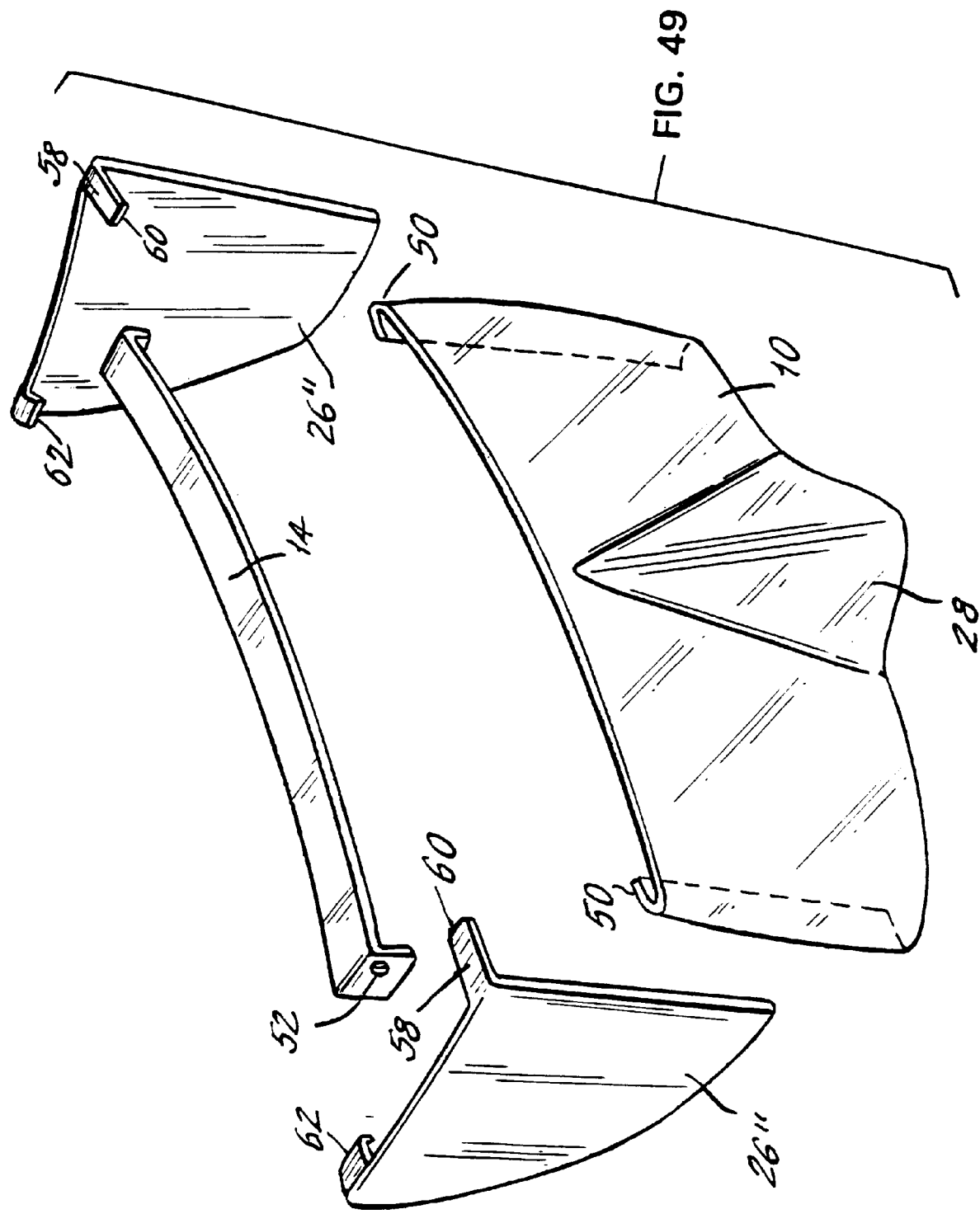

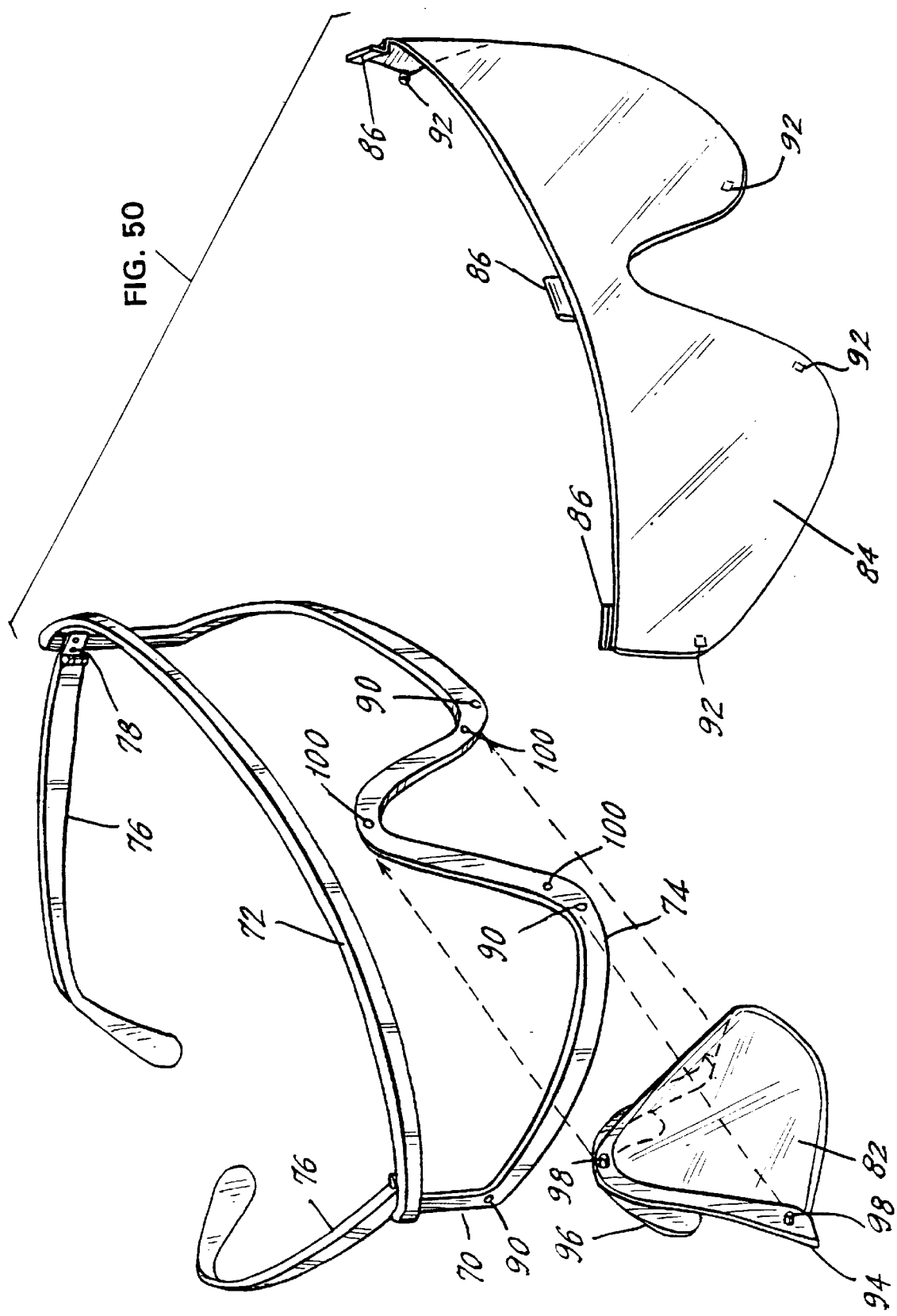

FACIAL SHIELD, PARTICULARLY FOR PROTECTION FROM THE SUN

This is a Continuation of application Ser. No. 08/366,895, filed on Dec. 30, 1994, now abandoned, which is a continuation of application Ser. No. 08/055,040, filed Apr. 29, 1993, now U.S. Pat. No. 5,379,464, which in turn is a continuation-in-part of application Ser. No. 07/919,587, filed Jul. 24, 1992, now U.S. Pat. No. 5,379,463.

BACKGROUND OF THE INVENTION

The present invention relates to a facial shield, and particularly, a facial shield for protection from damaging radiation from the sun. The invention also has applications as a facial shield for protection from the wind and also from flying objects, i.e., as an industrial facial shield, but is particularly applicable as a facial shield for protection from solar rays. The present invention thus provides the function available from what is commonly known as sunglasses, but also fulfills additional facial protective functions such as protecting the very sensitive and easily sunburned areas of the face, such as the nose and cheeks. The present invention is useful particularly in situations where there is substantial risk of overexposure to the sun's rays, and thus is useful in preventing sunburns and skin cancers caused by such overexposure.

Various forms of sunglasses and protective eyewear have been developed in the past. Applicant is aware of the following patents relating to sunglasses and protective eyewear:

U.S. Pat. Nos. 4,271,538; 4,976,530; 4,835,796; 4,507,809; 4,649,577; 4,991,952; 4,843,655; 4,527,291; Des. 314,391; Des. 294,952; Des. 314,001; Des. 321,703; Des. 322,616; 3,155,982; 3,233,249; 3,233,250; 3,384,903; 4,674,851; 4,730,915; 4,741,611; 4,824,233; 4,859,048; 4,867,550; 4,877,320; 4,951,322; 4,101,980.

None of these patents, however, provide a facial shield for protecting not only the eyes of the wear, but the other facial features which are at risk of receiving damaging radiation from the sun or at risk of being injured by flying objects or the wind.

SUMMARY OF THE INVENTION

Accordingly, it is an object of the present invention to provide a facial shield.

It is yet still a further object of the invention to provide a facial shield which protects a wearer from solar rays and/or which attenuates the intensity of solar radiation.

It is a further object of the invention to provide a functional and acceptable cosmetic device for the protection of the central facial area against ultraviolet light (30% of all skin cancers occur on the nose and 8% around the eyes).

Ultraviolet light (UV) is a known cause of skin cancer as well as premature aging of the skin (i.e. wrinkles, dark spots, rough spots, broken blood vessels). The UVB spectrum (290–320 nanometers) causes the most change with a lesser contribution from the UVA range (320–400 nanometers).

There appears to be a relationship between UV light and eye cataract formation and other chronic eye conditions (up to 520 nanometers—blue light).

Accordingly, it is a further object of the invention to provide protection against UVB (290–320 nanometers), protection against UVA (320–400 nanometers) and protection against blue light (400–520 nanometers).

It is yet still a further object of the present invention to provide a facial shield which protect not only the wearer's eyes, but other facial features, including the nose, cheeks and temples, and which prevents damaging radiation from reaching the wearer's eyes and other facial features both directly and from the side of the head.

It is yet still a further object of the present invention to provide a facial shield for protecting a wearer's face from windburn and from damaging flying objects.

The above and other objects of the present invention are achieved by facial protective wear comprising a facial shield member having a substantially transparent portion for allowing visible light to pass to the wearer's eyes; means coupled to the facial shield for supporting the facial shield on the wearer's head; the facial shield member further comprising a nose protective portion extending over and protecting substantially the wearer's entire nose from in front and above; and side portions protecting the wearer's eyes in a direction from the sides of the wearer's head. Preferably, the transparent portion substantially prevents passage of damaging ultraviolet radiation (UVA/UVB) and also lowers the intensity of solar radiation reaching the eyes and face.

The above and other objects of the invention are also achieved by facial protective wear comprising a facial shield member having a substantially transparent portion for allowing visible light to pass to the wearer's eyes; means coupled to the facial shield for supporting the facial shield on the wearer's head; the facial shield member further comprising a nose protective portion extending over and protecting substantially the wearer's entire nose from in front and from above. The nose protective portion may be made integral or removable, and the facial protective wear can be made in "clip-on" embodiments to attach removably to existing eyewear or hatwear.

The above and other objects of the invention are also achieved by a facial protective wear comprising a facial shield member having a substantially transparent portion for allowing visible light to pass to the wearer's eyes; means coupled to the facial shield member for supporting the facial shield on the wearer's head; and further comprising means for removably receiving a nose protective portion extending over and protecting substantially the wearer's entire nose from in front of and from above.

The above and other objects of the invention are furthermore achieved by a facial protective wear comprising a facial shield member having a substantially transparent portion for allowing visible light to pass to the wearer's eyes; means coupled to the facial shield member for supporting the facial shield member on the wearer's head, said means for supporting comprising a bridge bar disposed above the facial shield member and to which the facial shield member is coupled; temple bars pivotally attached to opposite ends of the bridge bar for providing support on the wearer's ears; and a lower frame contoured to the lower edge of the transparent portion of the facial shield member, and further comprising a nose protective portion extending over and protecting substantially the wearer's entire nose from in front of and from above, said nose protective portion being attached to said lower frame.

Other features and advantages of the present invention will become apparent from the following description of the invention which refers to the accompanying drawings.

BRIEF DESCRIPTION OF THE DRAWINGS

The invention will be described in greater detail in the following detailed description with reference to the drawings in which:

FIG. 5 is a side partially cross-sectional exploded view of the first embodiment, showing details of the coupling of temple bars according to the invention to the bridge portion of the first embodiment;

FIG. 6 is a side cross-sectional view of the transparent portion of the facial shield according to the first embodiment;

FIG. 7 is a side view of the transparent portion of the facial shield according to the first embodiment;

FIG. 8 is an exploded front view of the bridge and transparent portion of the facial shield according to the first embodiment.

FIG. 9 is a perspective front and side view of the facial shield according to the first embodiment;

FIG. 10 is an exploded detailed view of the means coupling the temple bar to the bridge portion of the facial shield according to the first embodiment;

FIG. 11 is a detailed view showing how a part of the transparent portion of the facial shield is attached to the bridge portion;

FIG. 12 shows how the transparent portion of the facial shield can be adjusted by the user;

FIG. 13 is a second embodiment of the facial shield according to the invention, showing an exploded rear perspective view;

FIG. 17 is a partial side cross-sectional view of the second embodiment;

FIG. 18 is a cross-sectional side view of the transparent shield portion of the second embodiment;

FIG. 19 is an exploded front view of the bridge and transparent portions of the facial shield of the second embodiment;

FIG. 24 is an exploded rear perspective view of the third embodiment;

FIG. 28 is an exploded rear perspective view of the fourth embodiment;

FIG. 29 is a top view of the fourth embodiment;

FIG. 30 is a side view of the fourth embodiment;

FIG. 31 is a front perspective view of the fourth embodiment;

FIG. 32 is a front view of the fourth embodiment;

FIG. 38 is a top view of a sixth embodiment;

FIG. 39 is a side view of the sixth embodiment;

FIG. 40 is a front perspective view of the sixth embodiment;

FIG. 41 is a front view of the sixth embodiment;

FIG. 47 is a front perspective view of an eighth embodiment;

FIG. 48 is a bottom exploded rear view of the eighth embodiment;

FIG. 49 is an exploded perspective front view of the eighth embodiment;

FIG. 50 is an exploded perspective view of a ninth embodiment;

DETAILED DESCRIPTION OF THE INVENTION

Figure 1:
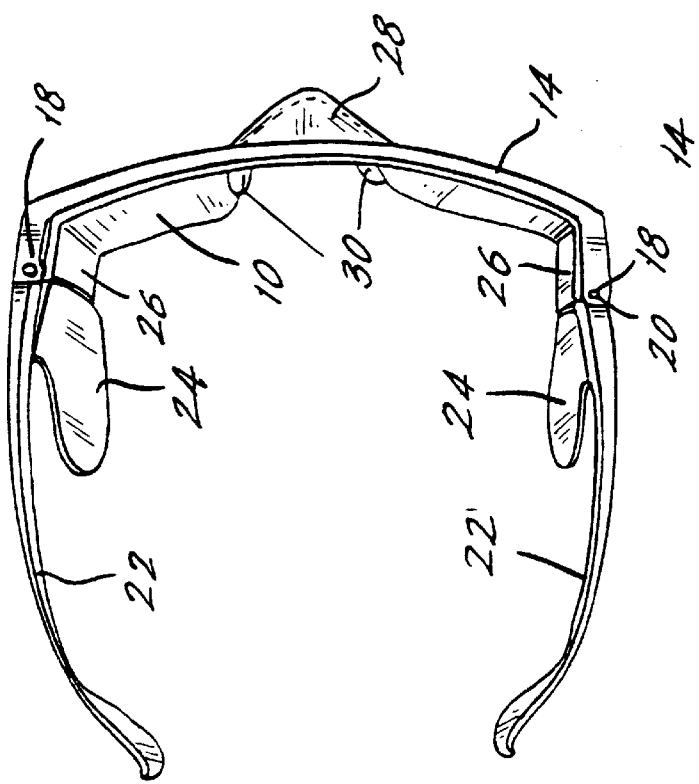
FIG. 1 is a top view of a first embodiment of a facial shield according to the invention.
Figure 2:
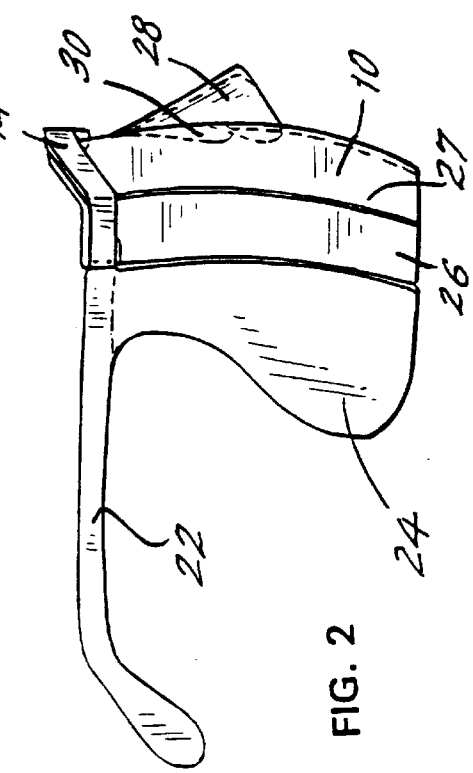
FIG. 2 is a side view of the embodiment of FIG. 1.
Figure 3:
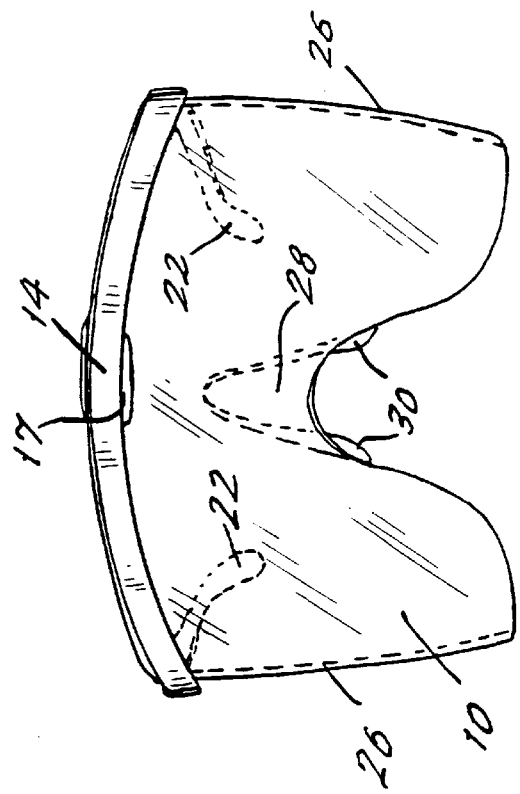
FIG. 3 is a front view of the first embodiment.
Figure 4:
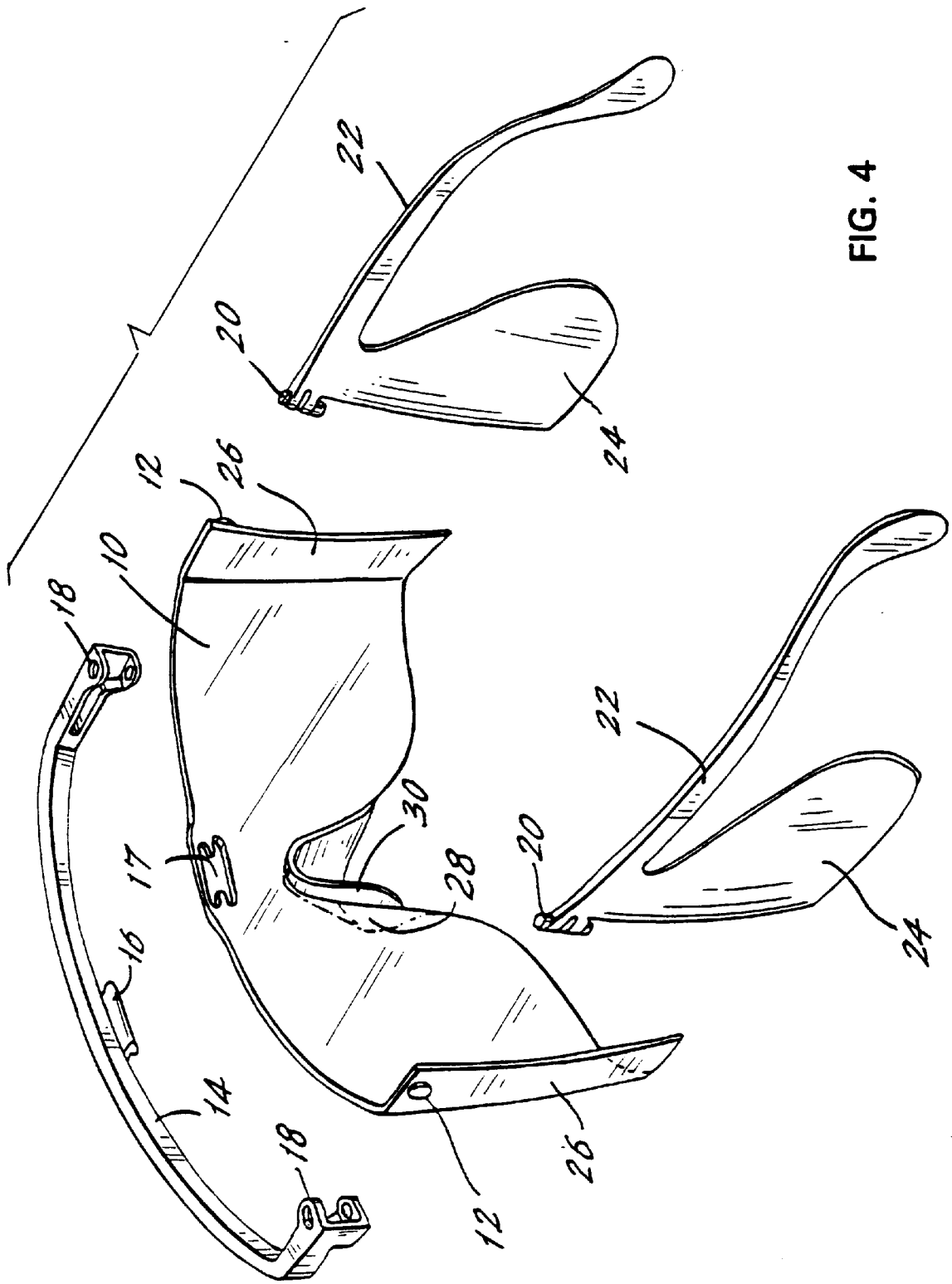
FIG. 4 is an exploded rear perspective view of the first embodiment.
Figure 16:
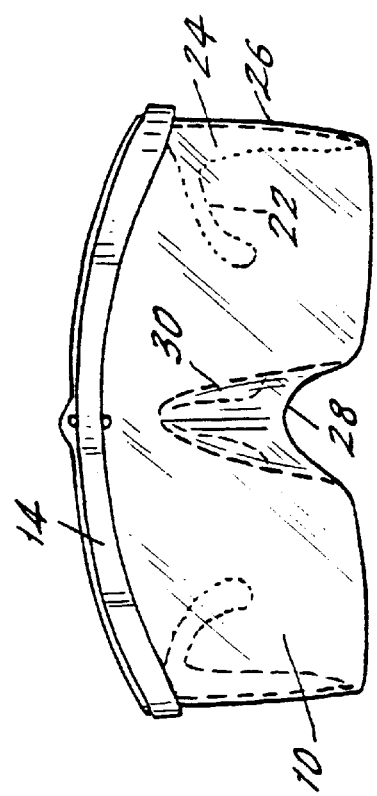
FIG. 16 is a front view of the second embodiment.
Figure 14:
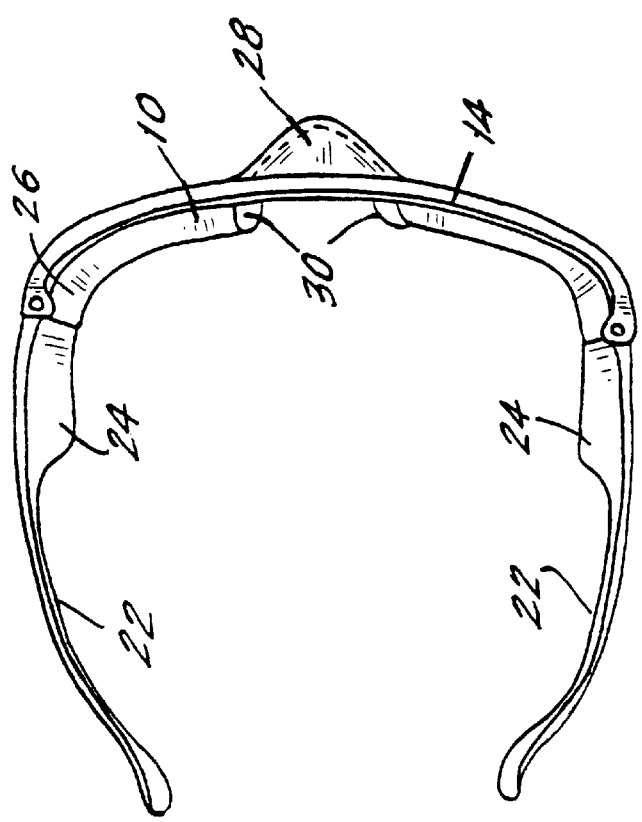
FIG. 14 is a top view of the second embodiment.
Figure 15:
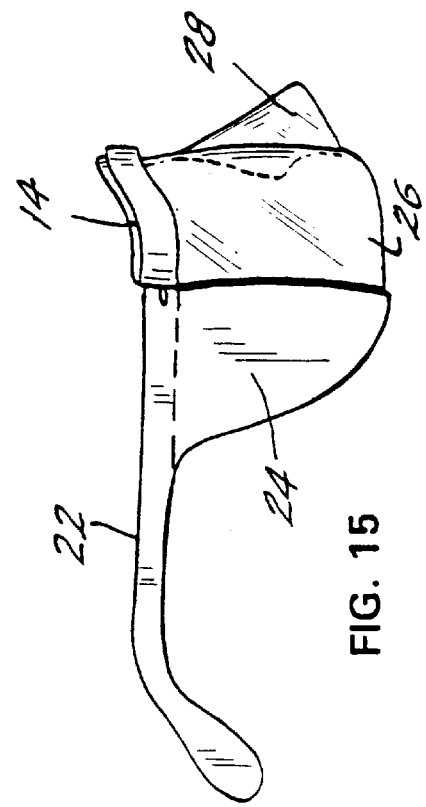
FIG. 15 is a side view of the second embodiment.
Figure 22:
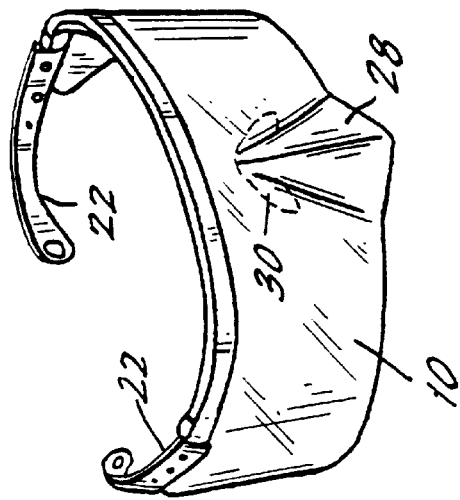
FIG. 22 is a front perspective view of the third embodiment.
Figure 23:
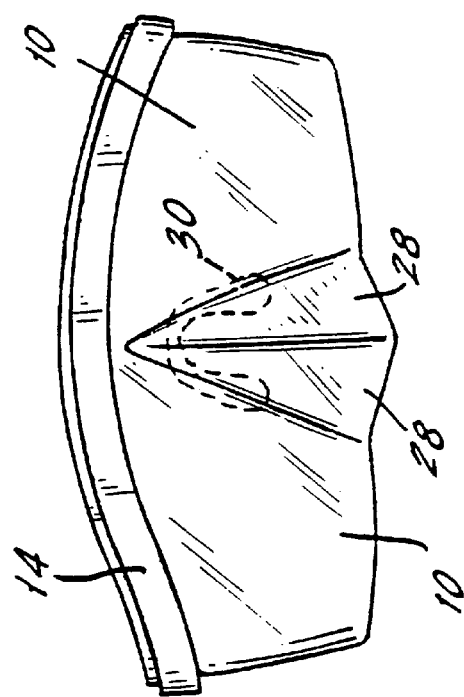
FIG. 23 is a front view of the third embodiment.
Figure 20:
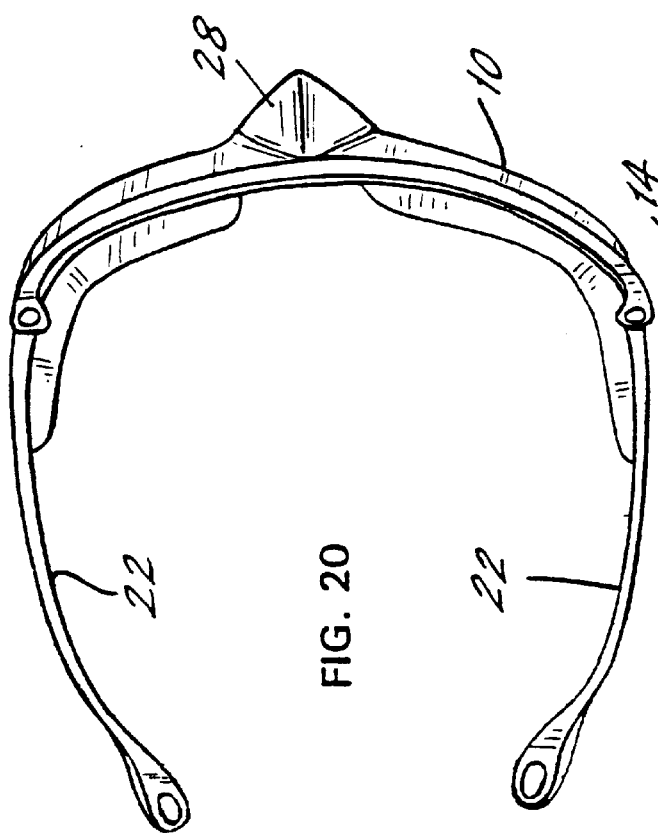
FIG. 20 is a top view of a third embodiment.
Figure 21:
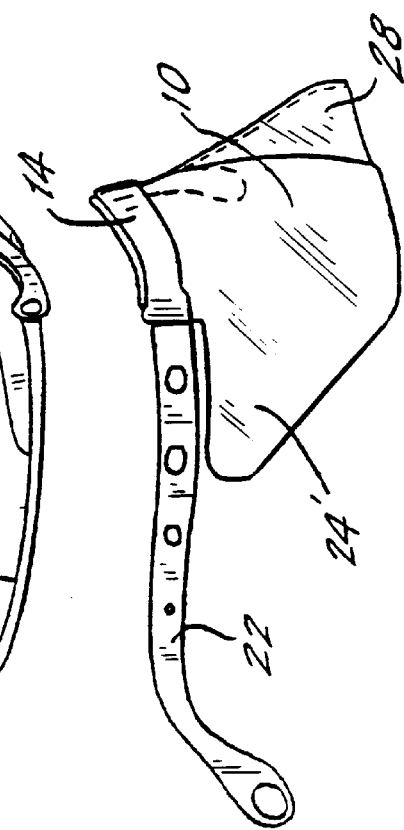
FIG. 21 is a side view of the third embodiment.
Figure 25:
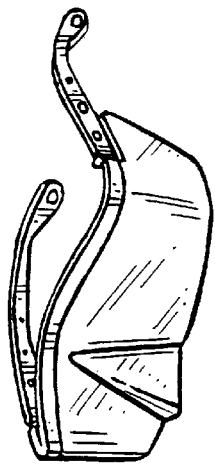
FIG. 25 is another front perspective view of the third embodiment.

With reference now to the drawings, various embodiments of facial shield according to the invention are shown. With reference to the different embodiments, like reference numerals will be used for like components even though the shape or configuration of the component may be changed in the different embodiments.

With reference to the drawing figures, the facial shield according to the invention includes a substantially transparent portion 10, which may be formed or molded of a suitable plastic material, for example polycarbonate. The transparent portion allows visible light to pass to the wearer's eyes and face, but substantially prevents damaging ultraviolet radiation from reaching the wearer's eyes and face, as well as substantially attenuating solar radiation passing to the wearer's face. The portion 10 may thus be suitably tinted or colored, and may be made large enough, as shown, to cover substantial portions of the wearer's cheeks, as well as the nose via a nose protective portion 28, to be described below.

In some embodiments, the shield includes pivot pins 12 disposed on each side of portion 10 for allowing pivoting of the portion 10 with respect to a bridge bar 14. The bridge bar 14 includes a means 16 for snapping into an opening 17 disposed in the transparent shield portion. The opening 18 may be formed as several selectible openings or otherwise suitably formed so as to allow the transparent shield portion to engage the bridge bar 14 at different positions, as will be explained below. The bridge bar 14 includes swivel sockets 18 disposed at each side for receipt of pivot pins 20 of temple bars 22. Preferably, the pivot pins 20 snap into the swivel holes 18 provided in the bridge bar 14. The bridge bar and temple bars are preferably molded of a suitable plastic material such as polycarbonate, for flexibility and strength. Preferably, pivot pins 20 are formed with ramped leading edges 21 (FIG. 10) to facilitate snap-in of the pins 20 into holes 18.

The temple bars 22 preferably include transparent wing portions 24, which are provided to shield the side of the wearer's face, for example, the temples, as well as the eyes, and particularly the outside corners of the eyes, from sunlight which comes from the side. The present invention, which can also be used as a facial shield for protecting the wearer from injury from wind or flying objects, is not limited to a facial shield for protecting the wearer's face and eyes from solar rays.

The transparent facial shield portion 10 of the first embodiment of FIGS. 1–12 also includes wrap-around side portions 26, which are provided to shield the wearer's eyes, particularly the outside corners of the eyes, from solar rays and/or flying objects and/or wind coming from the side.

In certain of the embodiments, the transparent shield portion 10 includes an integrally molded portion 28 for protecting substantially the wearer's entire nose from solar rays and/or flying objects. In other embodiments, as described below, the nose protective portion is removable from its position adjacent the transparent shield portion 10, as desired by the user. The transparent shield portion 10, adjacent the protective nose portion, is also provided with suitable padding or a nose conforming structure which supports the facial shield on the wearer's nose. This is indicated at 30.

As FIGS. 8, 10 and 11 show, in exploded views, the pivots 12 provided on the shield 10 snap into pivot points 32 provided on inward portions of the bridge bar 14. Details of the pivoting connection of the transparent shield 10 to the bridge bar 14 are shown in FIGS. 10 and 11. In particular, FIG. 11 shows a cross-section through a generally dovetailed slot 32 provided in the bridge bar. The transparent facial shield portion 10 preferably slides into the dovetailed slot 32 in area 33 prior to snapping of the pivot pins 20 into the holes 18 in area 35 of the bridge bar.

FIG. 12 shows how the transparent facial shield portion 10 may be adjusted with respect to the bridge bar 14, in order to adjust to the wearer's nose. The radius of adjustment is shown at R. The bridge bar includes a projection member 16 which snaps into any one of a number of separate or contiguous slots 17 provided in the transparent facial shield portion. This provides a radius of adjustment for the nose protective portion 28, centered on the pivot point 12, as shown in FIG. 12.

As shown, the invention provides a facial shield which protects those portions of the wearer's face which are most subject to injury from solar rays, wind or flying objects. The nose is protected by the protective portion 28, the wearer's cheeks are protected by the relatively large extent of the transparent facial shield portion 10 which extends down over the wearer's cheeks, and the sides of the wearer's face and temples, as well as the wearer's eyes from the side, are protected by the portions 26 of the transparent shield and the portions 24 of the temple bars 22.

FIGS. 13–19 show a second embodiment which is substantially the same as that shown in FIG. 1, although provided with differently shaped bridge bar, transparent shield portion and temple bars. As shown in the drawings of the second embodiment, the transparent facial shield portion 10 does not have a sharp corner (27 in the first embodiment) into the wrap-around portions 26 as in the first embodiment, but has a gradual curve 34 between the front portions of the shield portion 10 and the side portions 26.

Figure 26:
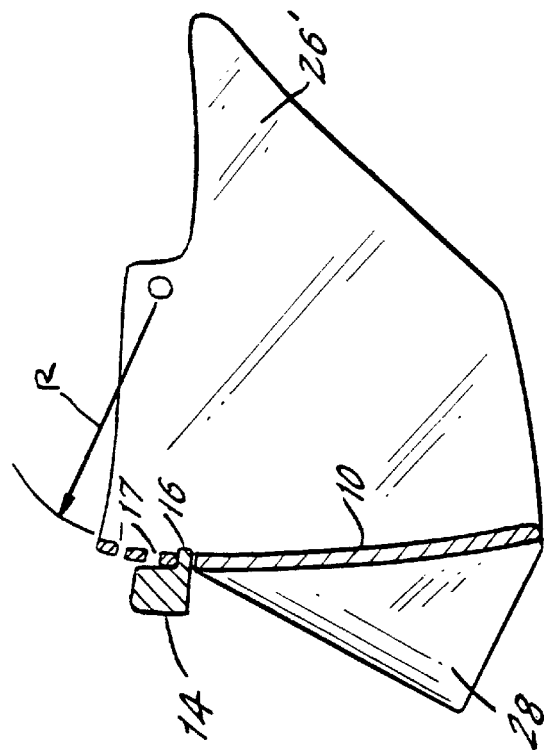
FIG. 26 is a side cross-sectional view of the third embodiment showing how the transparent portion of the facial shield can be adjusted by the wearer.
Figure 27:
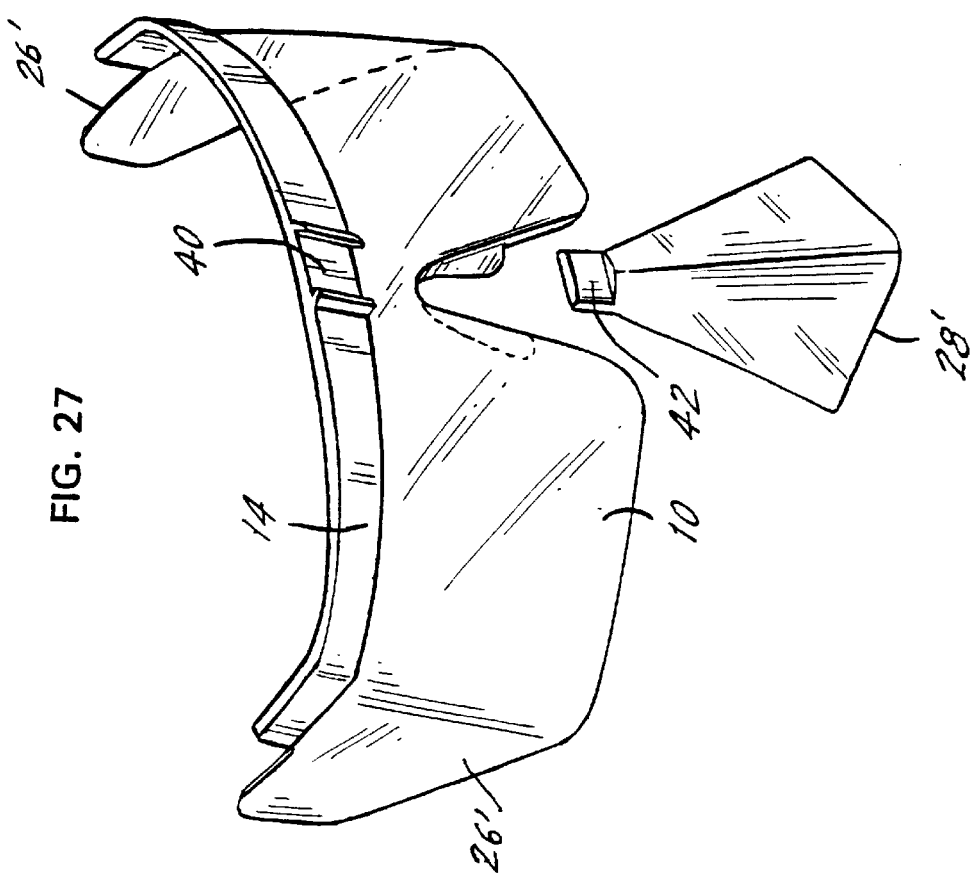
FIG. 27 is an exploded front perspective view of a portion of a fourth embodiment.
Figure 35:
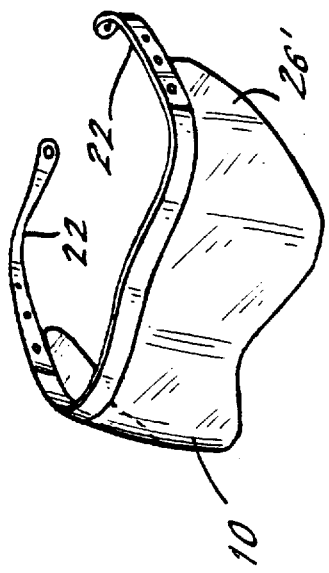
FIG. 35 is a front perspective view of the fifth embodiment.
Figure 36:
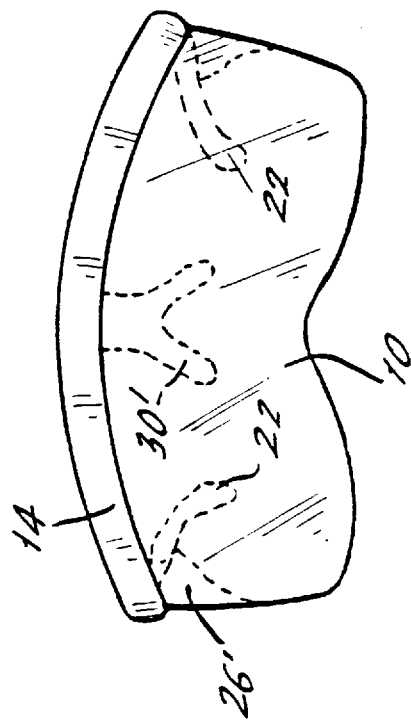
FIG. 36 is a front view of the fifth embodiment.
Figure 33:
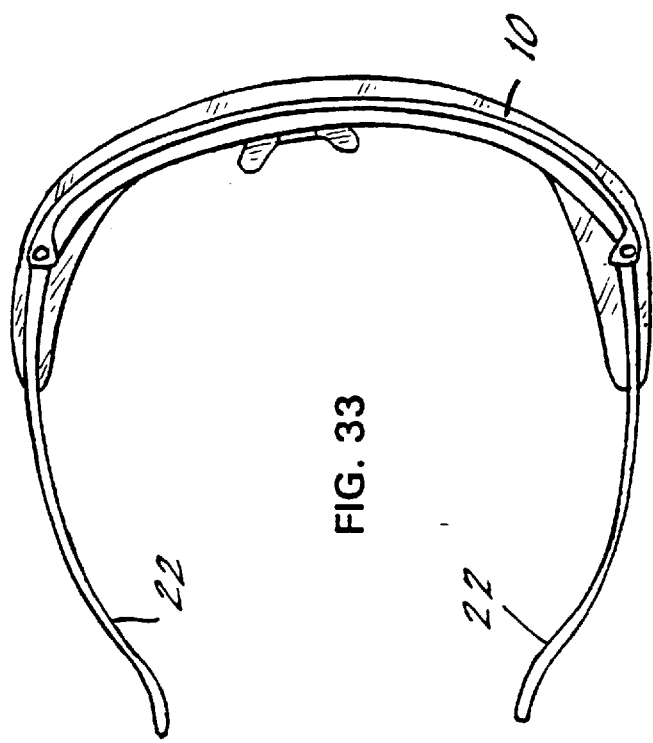
FIG. 33 is a top view of a fifth embodiment.
Figure 34:
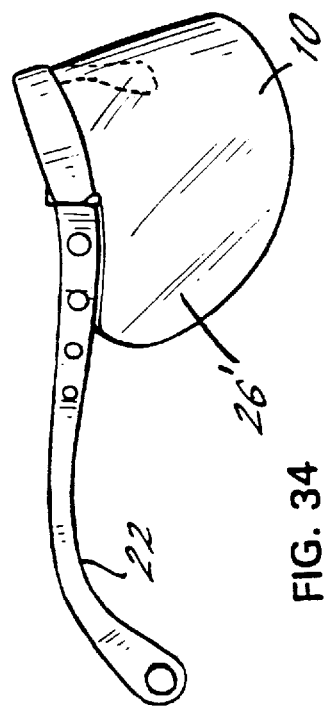
FIG. 34 is a side view of the fifth embodiment.

FIGS. 20–26 show a third embodiment of the invention, in which the transparent portions 10 extend continuously around the side of the wearer's face to the temple areas, forming side wings 24'. These side wings 24' accomplish the same function as the temple bar portions 24 of the previously described embodiments, but are instead formed integrally with the shield portion 10. FIG. 26 shows the manner in which the transparent facial shield portion 10 can be adjusted with respect to the bridge bar 14 in order to accommodate the wearer's nose comfortably.

FIGS. 27–32 show a fourth embodiment, which is provided with a clip-on nose protective portion 28' which can be removed. In this embodiment, the clip-on nose protective portion 28' clips into a channel 40 molded into the bridge bar 14. A suitable mating area 42 is provided on the nose protective portion 28'. Nose protective portion 28' can be transparent or it may be molded of an opaque material. Preferably it is a plastic material. The channel 40 may be dovetail shaped for holding the add-on nose protective cover 28'.

Figure 37:
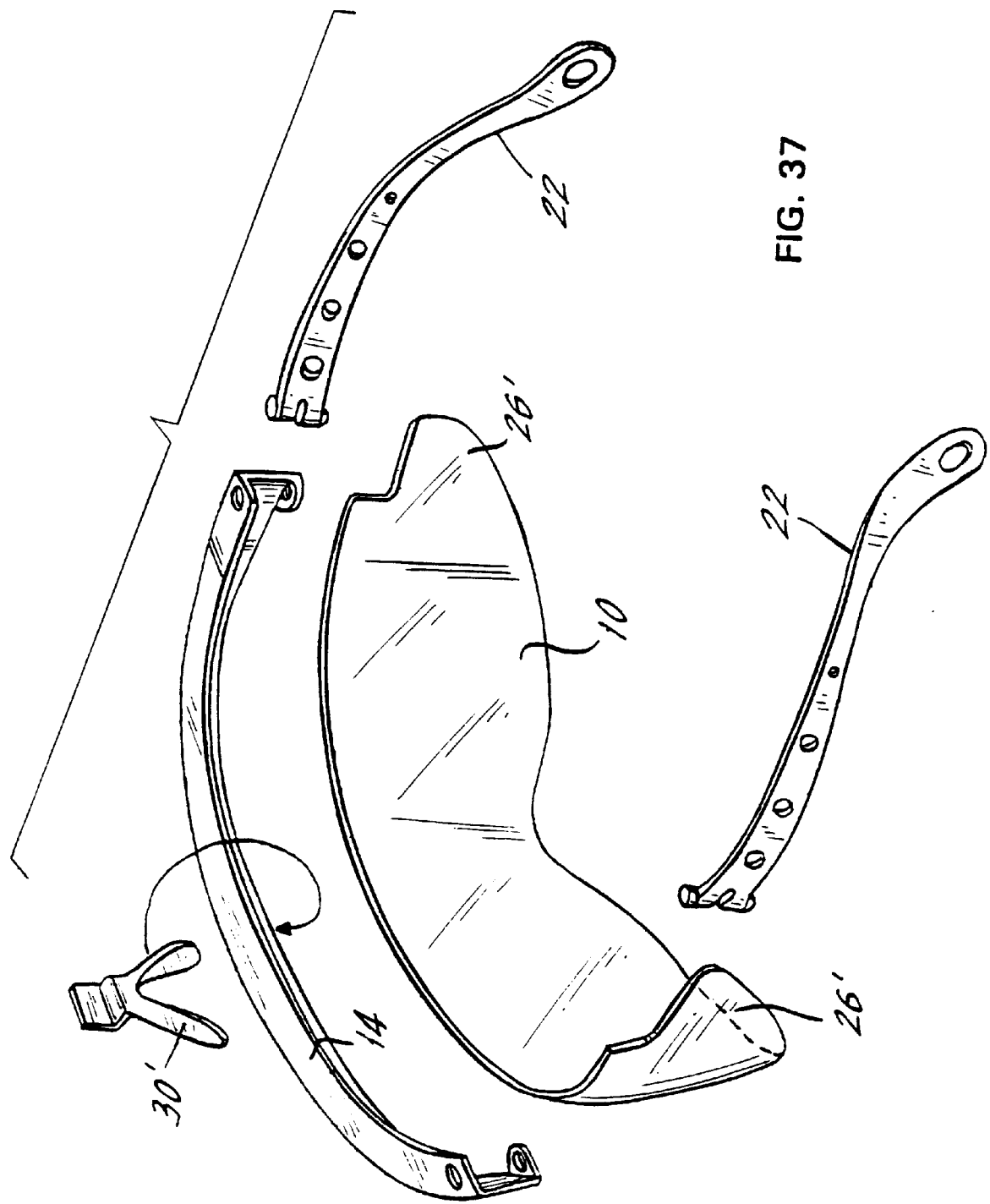
FIG. 37 is an exploded rear perspective view of the fifth embodiment.
Figure 42:
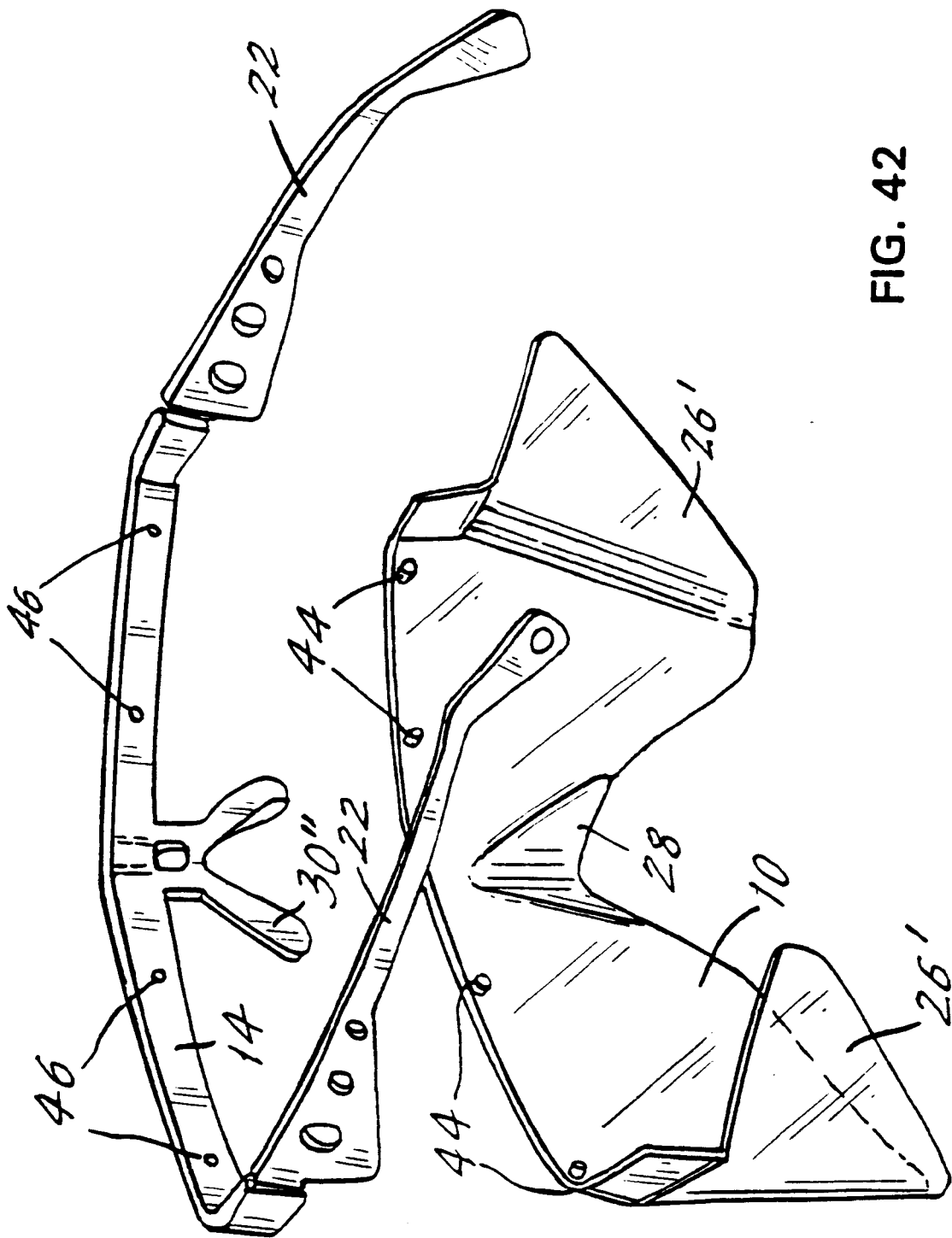
FIG. 42 is an exploded rear perspective exploded view of the sixth embodiment.

FIGS. 33–37 show a fifth embodiment wherein the transparent shield portion 10 is provided without a nose conforming protective portion. Instead, the transparent shield portion 10 projects outwardly and is molded as a continuous gradual compound wrap-around curve to shield the wearer's face, including the nose. The curve may be, and preferably is, both compound vertically and laterally. A nose support 30' is provided, which may be molded or clipped to the bridge bar 14 (or formed integrally or separately from shield portion 10), in order to support the shield on the wearer's face. As shown in FIG. 37, the nose support 30' can snap into place in the bridge bar 14. Preferably nose support 30' is made of clear plastic to minimize visual distraction as will be evident to a person of skill in the art, throughout the disclosure of the different embodiments according to the invention.

It should be understood that bridge bars 14 and temple bars 22 can be any color, they can be different colors and they can be suitably decorated. Also, transparent shield portion 10 can be provided with any suitable tint, or can be clear, as desired by choice or particular use.

FIGS. 38–42 show a sixth embodiment, which has a somewhat differently shaped transparent shield portion 10 and in which the bridge bar 14 is provided with an integrally molded nose support 30". In this version, the transparent shield portion 10 is provided with snap-in mounting posts 44 which are received in suitable mounting holes 46 provided in the bridge bar 14. The mounting posts 44 could alternatively be provided on the bridge bar, with the holes being provided in the portion 10.

The sixth embodiment is considered to be particularly adapted for protection from the wind, and thus is suggested for use as ski wear. The angular orientation of the members 10, 26 and 28 particularly conform to the wearer's facial planes and provide full nose and cheek coverage.

Figure 45:
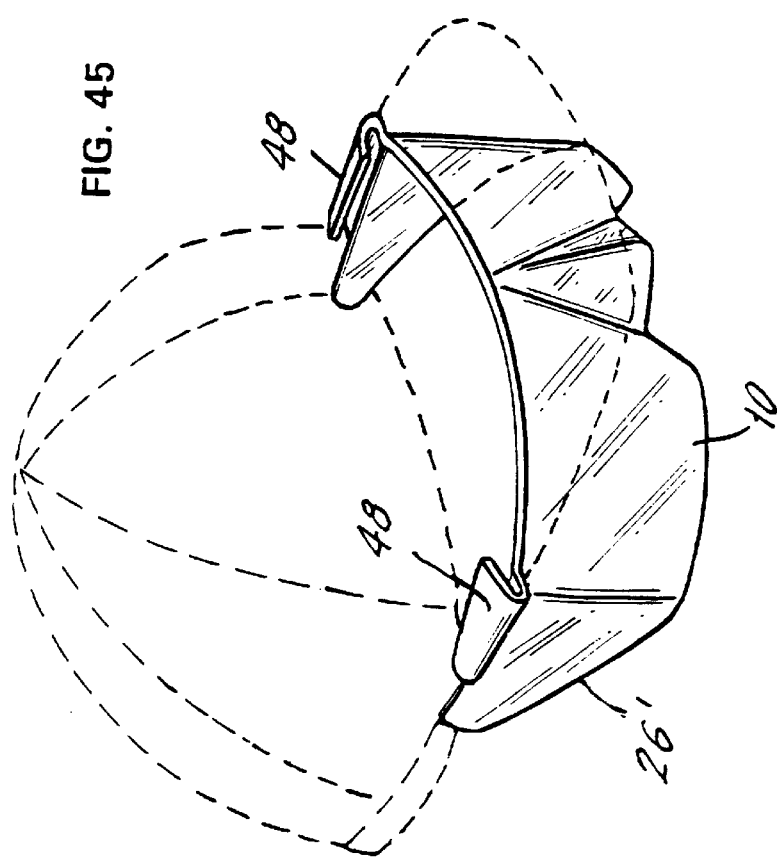
FIG. 45 is a front perspective view of the seventh embodiment.
Figure 46:
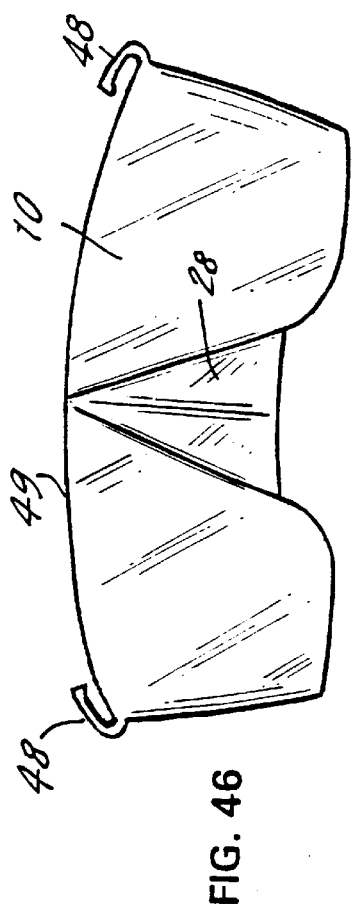
FIG. 46 is a front view of the seventh embodiment.
Figure 43:
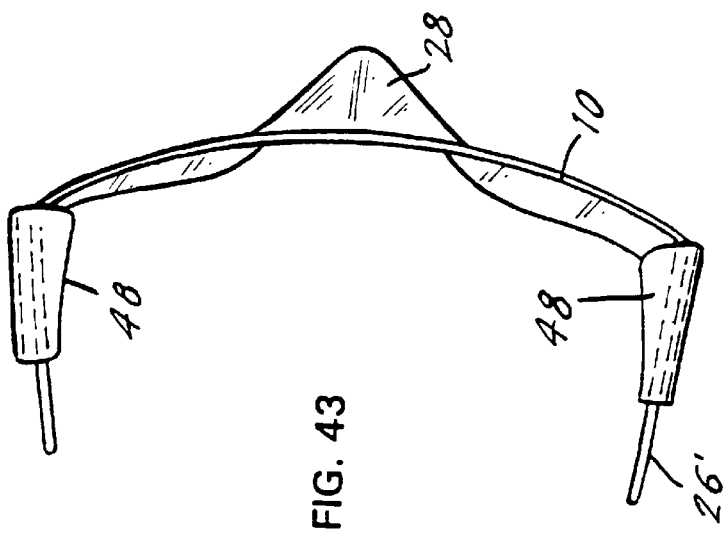
FIG. 43 is a top view of a seventh embodiment.
Figure 44:
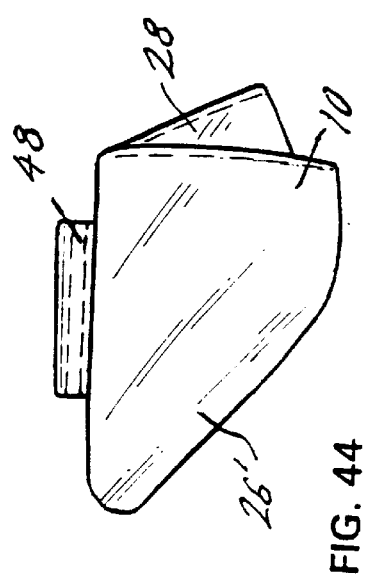
FIG. 44 is a side view of the seventh embodiment.

FIGS. 43–46 show a seventh embodiment which is provided to clip onto the visor of a hat, such as a baseball hat, as shown specifically in FIG. 45. Suitable clips 48 either integral with portion 10 or attached in any other way, are provided for receiving the visor of a hat. In this version, a bridge bar portion 14 is not necessary, nor are temple bars 22 required. A bridge bar could be provided, of course. Preferably, the embodiment of FIGS. 43–46 is of one piece, polycarbonate construction for flexibility and strength. The top curve 49 of the transparent portion 10 preferably is formed such that it sets the curve of the hat visor, e.g., a visor of a baseball hat, as shown in FIG. 45.

FIGS. 47–49 show an eighth embodiment of the invention, which is provided as a clip-on sun shield to be worn with a user's regular glasses or other eyewear, for example, prescription eyewear. A bridge bar 14 is provided in this embodiment, which receives the transparent facial shield portion 10 via pivot pins 50. The bridge bar portion 14 is provided with holes 52 at its ends to receive the pivot pins 50 to allow the shield portion 10 to pivot with respect to the bridge bar. Side wings 26", provided with tabs 58, shown specifically in FIG. 48, clip into overlapping guides 54 provided on the bottom of the bridge bar 14. Suitable adjustment ridges 56 molded in the bottom of the bridge bar 14 allow snap-in adjustment of tabs 58 to accommodate the outward extent of the wing portions 26". As shown in FIG. 49, extending tabs 58 of the wing portions 26", are each provided with a ridge 60 at their inwardmost extent for engaging with selected ones of the ridges 56 on the bridge bar 14. The embodiment of FIGS. 47–49 is thus adaptable to the normal eyewear of different wearers. The wing portions 26" are provided with clips 62 for clipping on to the temple bars of the wearer's normal eyewear.

The pivot pins 50 of the shield 10 and holes 52 in the bridge bar 14 allow the shield 10 to flip up out of the wearer's view, as desired.

Figure 51:
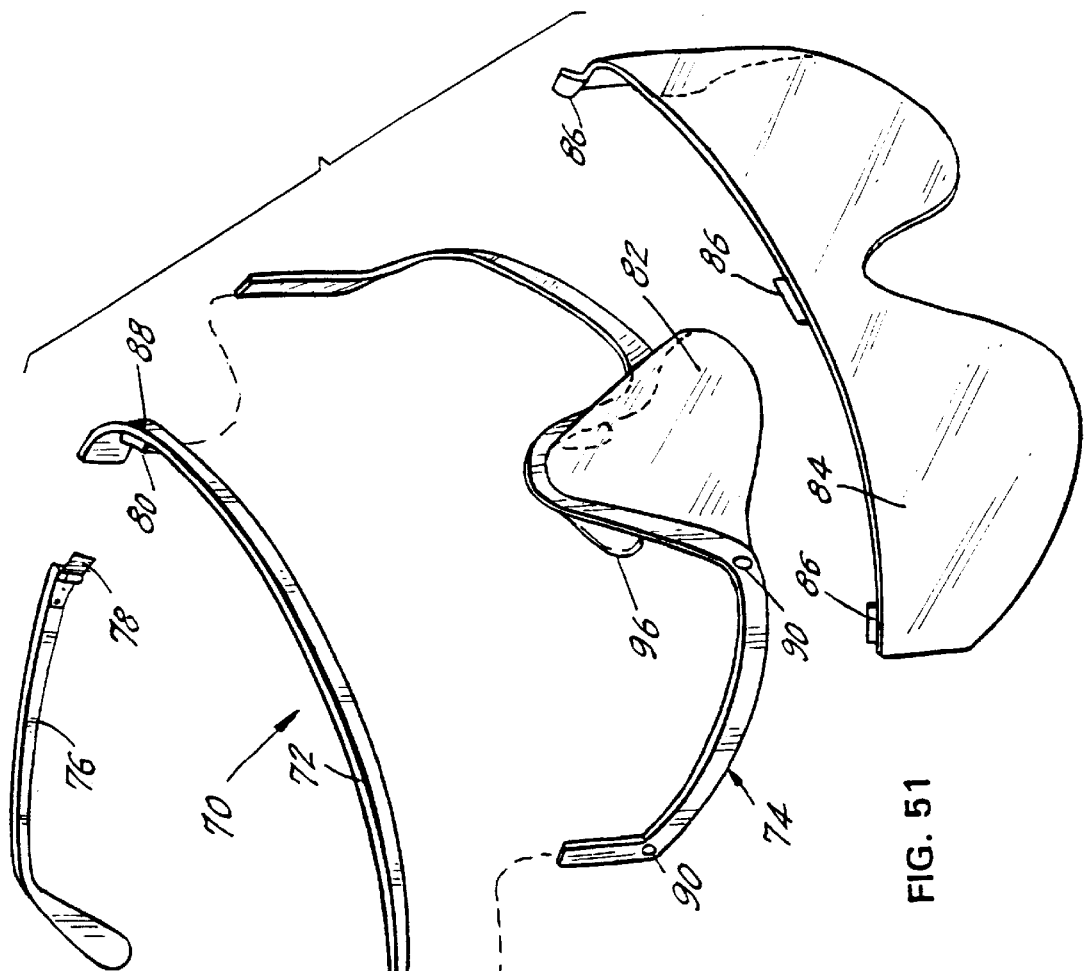
FIG. 51 is an exploded perspective view of the ninth embodiment showing further details of that embodiment.

FIGS. 50 and 51 show a ninth embodiment of the present invention. As shown in these figures, the facial shield includes a frame 70, the frame 70 including a bridge portion 72 and lower frame portion 74. Two temple bars 76 are hingedly attached to the bridge portion at 78. The lower frame portion 74 is joined to the bridge portion 72 at points 80. For example, a sliding fit of the lower frame portion 74 to the bridge portion 72 may be provided. After the lower frame portion 74 is joined to the bridge portion 72, they can be shoot molded so the two parts 74 and 72 are integral. As shown, a sliding fit onto posts 80 on the bridge portion 72 will allow securement of the portion 74 to the bridge portion 72 prior to molding to make the two pieces integral.

The nose protective member 82 may be transparent (clear or tinted) or opaque, and preferably is secured to the lower frame portion 74, either as a separate piece, or integrally molded with the frame portion 74. The transparent shield portion 84 is secured to the bridge portion 72 by suitable extensions 86, which are received in recesses 88 in the back of the bridge portion 72, for example, a snap-fit.

The bridge portion 74 may be provided with suitable apertures 90 which receive posts 92 provided on the transparent shield portion 84 so that the posts 92 snap into the apertures 90, thereby securing the shield portion to the frame portion 74 after the shield portion 84 extensions 86 are snapped into the recesses 88 in the bridge portion 72.

The embodiment shown in FIGS. 50 and 51 may be provided with a removable nose piece 82, which includes its own frame 94 as well as a nose supporting member 96. If the nose protective portion is removable, it may be secured removably to the frame portion 74 by suitable posts 98 molded into the frame portion 94 and which are receivable in apertures 100 provided in the frame portion 74.

Figure 52:
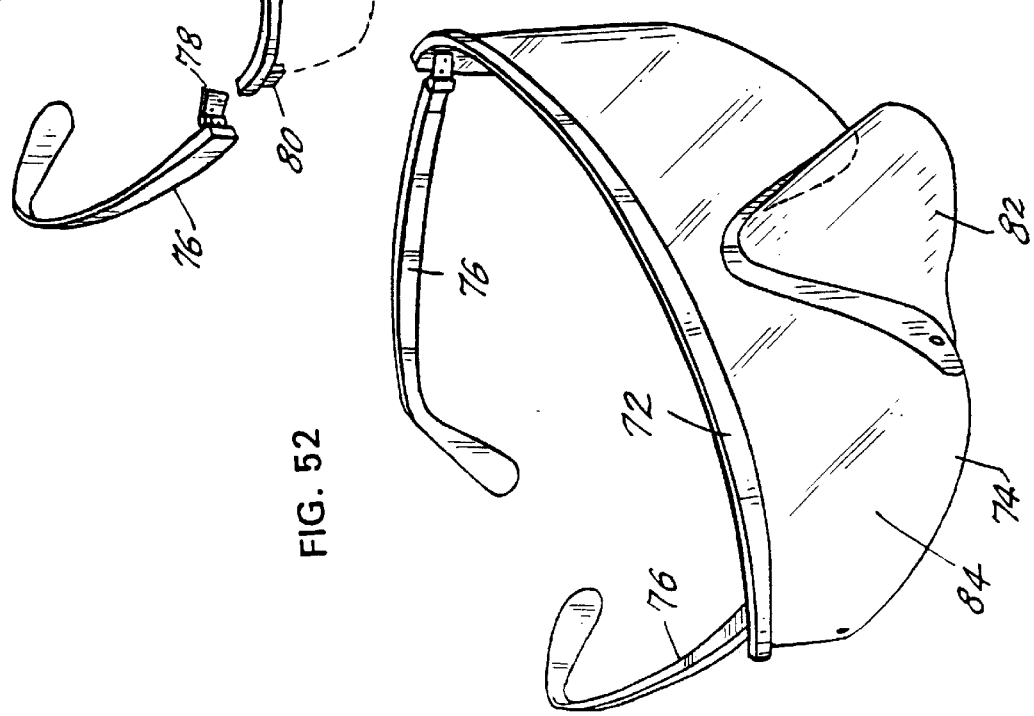
FIG. 52 is a perspective view of a tenth embodiment.
Figure 53:
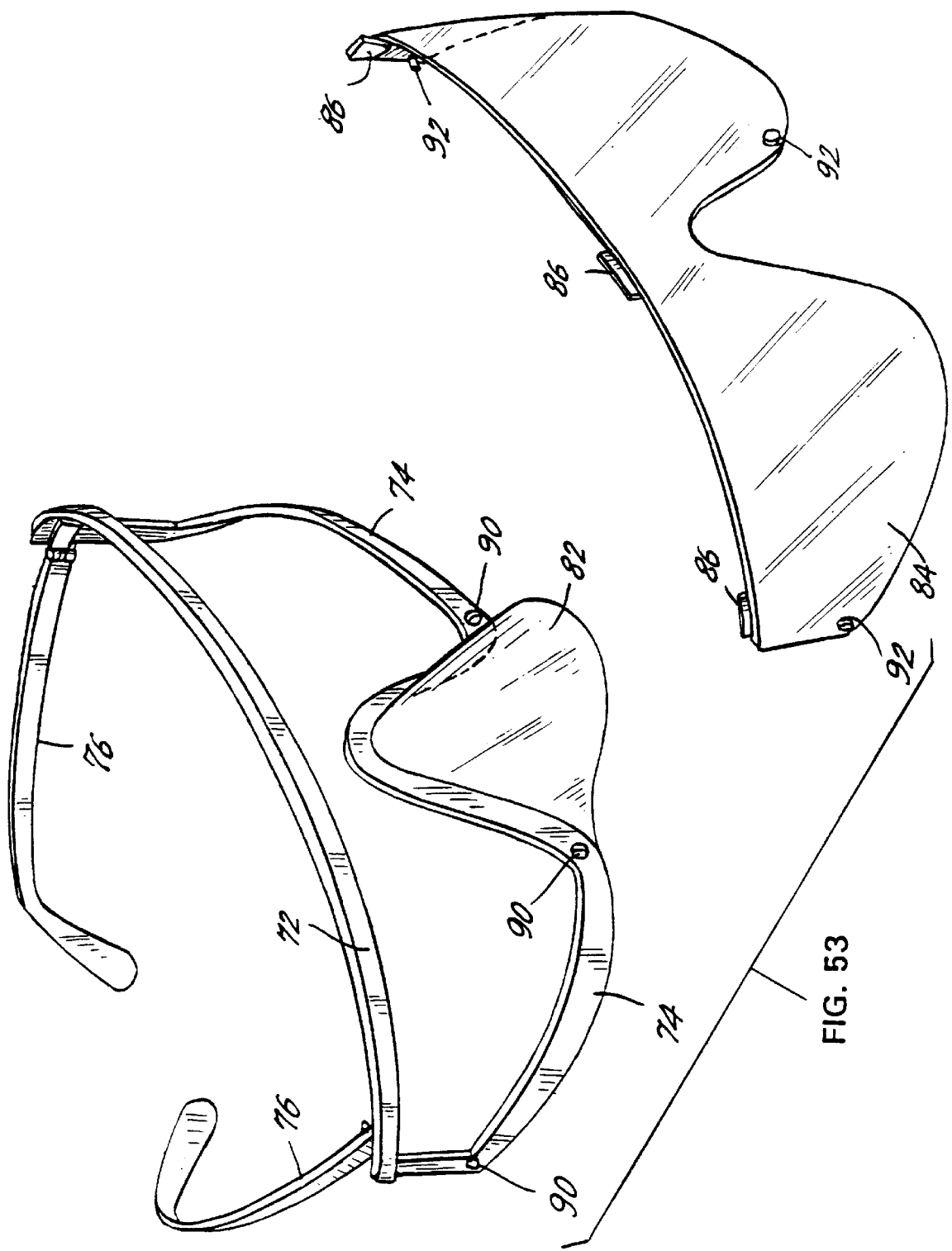
FIG. 53 is an exploded perspective view of the tenth embodiment.

FIGS. 52 and 53 show a tenth embodiment of the present invention. This embodiment is similar to the embodiment of FIGS. 50 and 51, having a bridge portion 72, lower frame portion 74, temple members 76 and transparent shield portion 84. In this embodiment, however, the nose protective portion 82 is permanently attached to the lower frame portion 74, and may be made integrally therewith or as a separately attached piece.

Preferably in both embodiments shown in FIGS. 50–53, the transparent shield portion 84 is also removable, snap fitting into the frame via the extensions 86 and posts 92. In this way, different color/shading options can be provided so that the user can exchange the transparent shield portion with one of another shading or color.

There has thus been described a novel facial shield for protection of a large portion of the wearer's face, including the eyes, nose, cheeks and side portions of the head, and which prevents, if used and adapted as protection from the sun, solar rays from reaching these areas from the front and from reaching these areas from the side of the wearer's face. The device of the invention can also be used as a facial shield for protection from the wind or from injury from flying objects, i.e., for use as an industrial protective shield.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. Facial protective wear comprising:
    a facial shield member having a substantially transparent portion for allowing visible light to pass to the wearer's eyes;
    the facial shield member including wing members each protecting a portion of respective sides of the wearer's head; and
    a clip comprising a U-shaped channel coupled to each wing member for fastening the facial shield member to an edge of a visor of a hat worn by the wearer and for supporting the facial protective wear on the hat; the U-shaped channel of each wing member having an opening into the U-shaped channel for receiving the edge of the visor of the hat, the opening of each U-shaped channel facing the opening of the opposite U-shaped channel of the other wing member thereby to receive the visor between the U-shaped channels.

2. The facial protective wear recited in claim 1, further comprising:
    a nose protective portion extending over and protecting substantially the wearer's entire nose from in front and from above.

3. The facial protective wear recited in claim 2 wherein the nose protective portion is removable.

4. The facial protective wear recited in claim 1, wherein the channel is integrally molded to the facial shield member for receiving an edge of the visor of the hat.

5. The facial protective wear recited in claim 1, wherein the transparent portion prevents transmission of a substantial portion of ultraviolet solar radiation.

6. Facial protective wear comprising:
    a facial shield member having a substantially transparent portion for allowing visible light to pass to the wear's eyes, the facial shield member including wing members each protecting a portion of respective sides of the wearer's head; and a clip comprising a U-shaped channel coupled to each wing member of the facial shield member for fastening the facial shield member to a wearer's eyewear, the clip attaching the facial shield member to temple bars of the wearer's eyewear and for supporting the facial shield member on the wearer's eyewear, each U-shaped channel having an opening into the U-shaped channel for receiving a respective temple bar of the wearer's eyewear, the opening facing downwardly when the facial protective wear is worn by the wearer.

7. The facial protective wear recited in claim 6, wherein the transparent portion prevents transmission of a substantial portion of ultraviolet solar radiation.

8. The facial protective wear recited in claim 6, further comprising:

a nose protective portion extending over and protecting substantially the wearer's entire nose from in front and from above.

9. The facial protective wear of claim 6, further comprising a bridge bar above the facial shield member, the bridge bar having a lower surface in engagement with a top portion of a wearer's eyewear for supporting the facial protective wear on the wearer's eyewear.

10. Facial protective wear comprising:

a facial shield member having a substantially transparent portion for allowing visible light to pass to the wear's eyes; and at least one clip coupled to the facial shield member for fastening the facial shield member to a wearer's eyewear, each clip attaching the facial shield member to temple bars of the wearer's eyewear and for supporting the facial shield member on the wearer's eyewear;

the facial shield member including wing members each protecting a portion of respective sides of the wearer's head, each clip being attached to each of said wing members for attaching the facial shield member to temple bars of the wearer's eyewear for supporting the facial shield member on the wearer's eyewear; and further comprising a bridge bar disposed above the facial shield member and to which the facial shield member is coupled, the wing members being adjustably laterally connected to the bridge bar through a projection slidable in a channel so as to move toward or away from the side of the wearer's head to accommodate different wearers.

\* \* \* \* \*